ˍˍˍˍˍˍˍˍˍˍˍˍˍˍˍˍˍˍˍˍˍˍˍˍˍ US011097017B2

(12) United States Patent
Preihs et al.

(10) Patent No.: US 11,097,017 B2
(45) Date of Patent: *Aug. 24, 2021

(54) GADOLINIUM-BASED CONTRAST AGENTS FOR SENSITIVE DETECTION OF $ZN^{2+}$ WITH MRI

(71) Applicant: The Board of Regents of the University of Texas System, Austin, TX (US)

(72) Inventors: Christian Preihs, Dallas, TX (US); Jing Yu, Coppell, TX (US); Veronica Clavijo Jordan, Dallas, TX (US); Yunkou Wu, Coppell, TX (US); Khaled Nasr, Dallas, TX (US); A. Dean Sherry, Dallas, TX (US); Sara Chirayil, Plano, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/246,890

(22) Filed: Jan. 14, 2019

(65) Prior Publication Data

US 2019/0142977 A1 May 16, 2019

Related U.S. Application Data

(63) Continuation of application No. 15/126,632, filed as application No. PCT/US2015/019928 on Mar. 11, 2015, now Pat. No. 10,207,013.

(60) Provisional application No. 61/954,474, filed on Mar. 17, 2014.

(51) Int. Cl.
*A61K 49/10* (2006.01)
*C07D 213/38* (2006.01)
*A61B 5/055* (2006.01)

(52) U.S. Cl.
CPC ............ *A61K 49/108* (2013.01); *A61B 5/055* (2013.01); *A61K 49/106* (2013.01); *C07D 213/38* (2013.01)

(58) Field of Classification Search
CPC ......... A61K 49/00; A61K 49/10; A61B 5/055
See application file for complete search history.

(56) References Cited

U.S. PATENT DOCUMENTS 8,580,231 B2 * 11/2013 Sukerkar .............. A61K 49/14
424/9.363
8,679,453 B2 3/2014 De Leon-Rodriguez
9,339,563 B2 5/2016 De Leon-Rodriguez
10,207,013 B2 * 2/2019 Preihs ............... A61K 49/106
2006/0057062 A1 3/2006 Trotter
2011/0009605 A1 * 1/2011 De Leon-Rodriguez ............
C07F 5/003
534/10
2014/0081009 A1 3/2014 De Leon-Rodriguez

FOREIGN PATENT DOCUMENTS

WO WO 2002/043775 6/2002
WO WO 2008/134289 11/2008

OTHER PUBLICATIONS

Krisada Kittigowittana et al., Development of Intravascular Contrast Agents for MRI Using Gadolinium Chelates, ChemMedChem, 6, 781-787. (Year: 2011).*
Clavijo Jordan et al., "Zinc-sensitive MRI contrast agent detects differential release of Zn(II) ions from the healthy vs. malignant mouse prostate," *Proceedings of the National Academy of Sciences of the USA*, 113(37):E5464-E5471, 2016.
Esqueda et al., "A New gadolinium-based MRI zinc sensor," *J. Am. Chem. Soc.*, 131(32):11387-11391, 2009.
Ferreira et al., "Gd(DO3A-N-α-aminopropionate): a versatile and easily available synthon with optimized water exchange for the synthesis of high relaxivity, targeted MRI contrast agents," *Chem. Commun.*, 42:6475-6477, 2009.
Hirayama et al., "Selective labeling of tag-fused protein by tryptophan-sensitized luminescence of a terbium complex," *Chem. Commun.*, 3196-3198 and Supplementary Information, 2009.
Jászbérenyi et al., "Fine-tuning water exchange on $Gd^{III}$ poly(amino carboxylates) by modulation of steric crowding," *Dalton Trans.*, 16:2713-2719, 2005.
Kittigowittana et al., "Development of intravascular contrast agents for MRI using gadolinium chelates," *ChemMedChem*, 6:781-787, 2011.
Office Communication issued in U.S. Appl. No. 15/126,632, dated Oct. 19, 2017.
PCT International Preliminary Report on Patentability issued in International Application No. PCT/US2015/019928, dated Sep. 29, 2016.
PCT International Search Report and Written Opinion issued in International Application No. PCT/US2015/019928, dated Jun. 3, 2015.
Woods and Sherry, "Synthesis and luminescence studies of aryl substituted tetraamide complexes of europium(III): a new approach to pH responsive luminescent europium probes," *Inorg. Chem.*, 42:4401-4408, 2003.

(Continued)

*Primary Examiner* — Michael G. Hartley
*Assistant Examiner* — Jagadishwar R Samala
(74) *Attorney, Agent, or Firm* — Parker Highlander PLLC

(57) ABSTRACT

In some aspects, the present disclosure provides novel ligands, which may be used to make novel MRI contrast agents for the detection of zinc. In further aspects, by the present disclosure also provides methods of using as imaging agents and compositions thereof.

16 Claims, 11 Drawing Sheets

(56) References Cited

OTHER PUBLICATIONS

Yu et al., "Amplifying the sensitivity of zinc(II) responsive MRI contrast agents by altering water exchange rates," *J. Am. Chem. Soc.*, 137:14173-14179, 2015.

Yu et al., "New gadolinium-based contrast agents for highly sensitive detection of Zn(II) with MRI," Poster, 247th ACS National Meeting, Dallas, Texas, Mar. 18, 2014.

* cited by examiner

GADOLINIUM-BASED CONTRAST AGENTS FOR SENSITIVE DETECTION OF ZN$^{2+}$ WITH MRI

This application is a continuation of U.S. application Ser. No. 15/126,632, filed Sep. 16, 2016, which is a national phase application under 35 U.S.C. § 371 of International Application No. PCT/US2015/019928, filed Mar. 11, 2015, which claims benefit of priority to U.S. Provisional Application Ser. No. 61/954,474 filed Mar. 17, 2014, the entire contents of each of which are hereby incorporated by reference.

This invention was made with government support under Grant No. RO1DK095416 awarded by the National Institutes of Health. The government has certain rights in the invention.

BACKGROUND

1. Field

The present disclosure relates generally to the fields of diagnostic testing and imaging agents. The disclosure provides, for example, novel ligands for the preparation of MRI imaging agents, novel MRI imaging agents, compositions of the novel imaging agents, and methods of use thereof.

2. Description of Related Art

Molecular imaging is used for visualizing biological targets and to understand their complexities for diagnosis and treatment purposes. Through an accurate and real-time imaging of biological targets, a thorough understanding of the fundamental biological processes can be gained leading to the successful diagnose of various diseases (Weissleder, 2006). In particular, MRI imaging can be useful to help visualize those biological processes.

Gadolinium is a known and well characterized Ticontrast agent with useful and important physical properties for use in MRI imaging agents. Unfortunately, this ion is highly toxic in a "free" state, and hence it is typically used as a thermodynamically stable and kinetically inert complex. Linear polyamine diethylenetriaminepentaacetic acid (DTPA) or polyazamacrocycle 1,4,7,-10-tetraazacyclododecane-1,4,7,10-tetraacetic acid derivatives (DOTA) with coordinating acetate arms have been commercially employed as they form sufficiently stable Gd(III) complexes. Unfortunately, these low molecular weight contrast agents are nonspecific, rapid renal excretion and extravasation, and they have relatively low relaxivity. Additionally, in order, to selectively target and identify other metal ions in solution additional functionality must be added to the contrast agent.

Zinc(II) ions in particular are of particular interest as zinc is the second most abundant trace element in mammalian tissues and plays an extensive role in controlling gene transcription and metalloenzyme function (Esqueda, et al., 2009). The prostate, pancreas, and brain are known to contain relatively large amounts of zinc ions relative to other issues in the body. Zinc and the movement of zinc ions has been associated with the formation of α-amyloids, the release of insulin by β-cells in the pancreas and changes in concentration in zinc is associated with formation of tumors particular in prostate tissue. As such, a method of in vivo imaging of zinc represents a key goal to helping understand these biological functions and associated disease states such as Alzheimer's disease, diabetes, and cancer.

Esqueda, et al. (2009) and US Patent Application 2011/0009605 reported an MRI based zinc targeting contrast agent which contained two dipicolylamine units conjugated to a Gd-chelated DOTA. This ligand in the presence of zinc shows increased relaxivity compared to the ligand without zinc present. Unfortunately, this particular ligand still has relatively low relaxivity giving and therefore a relatively high (~100 μM) detection limit and thus improvements in the relaxivity of the complex can greatly improve the detection limit of the contrast agent which would be useful in a larger variety of biological applications.

SUMMARY

In some aspects, the present disclosure provides compounds of the formula:

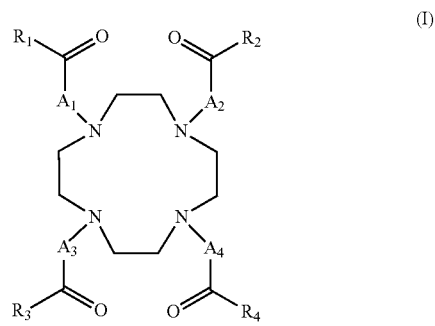

wherein: $A_1$, $A_2$, $A_3$, and $A_4$ are each independently alkanediyl$_{(C \leq 12)}$ or substituted alkanediyl$_{(C \leq 12)}$; and $R_1$, $R_2$, $R_3$, and $R_4$ are each independently hydroxy, amino, alkylamino$_{(C \leq 12)}$, substituted alkylamino$_{(C \leq 12)}$, dialkylamino$_{(C \leq 12)}$, substituted dialkylamino$_{(C \leq 12)}$, or

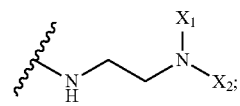

wherein: $X_1$ and $X_2$ are each independently heteroaralkyl$_{(C \leq 12)}$ or substituted heteroaralkyl$_{(C \leq 12)}$; provided that at least one of $A_1$, $A_2$, $A_3$, or $A_4$ is not —CH$_2$—; or a metal complex, a deprotonated form, or a salt thereof. In some embodiments, compound is further defined as:

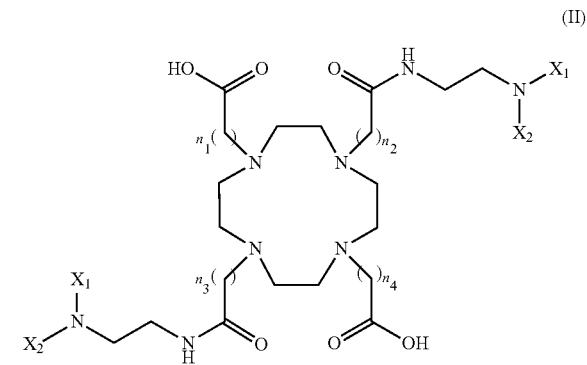

wherein: $n_1$, $n_2$, $n_3$, and $n_4$ are 1, 2, 3, 4, 5, 6, 7, or 8; and $X_1$ and $X_2$ are each independently selected from heteroaralkyl$_{(C \leq 12)}$ or substituted heteroaralkyl$_{(C \leq 12)}$; provided that at least one of $n_1$, $n_2$, $n_3$, and $n_4$ are not 1; or a metal complex, a deprotonated form or a salt thereof. In some embodiments, the formula is further defined as:

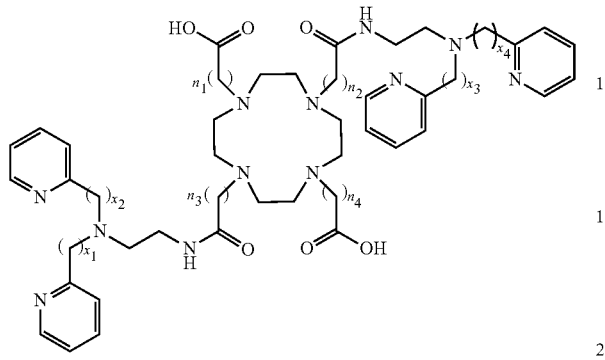

(III)

wherein: $n_1$, $n_2$, $n_3$, and $n_4$ are 1, 2, 3, or 4; provided that at least one of $n_1$, $n_2$, $n_3$, and $n_4$ are not 1; and $x_1$, $x_2$, $x_3$, and $x_4$ are 1, 2, 3, or 4; or a metal complex, a deprotonated form, or a salt thereof. In some embodiments, at least one of $R_1$, $R_2$, $R_3$, or $R_4$ is

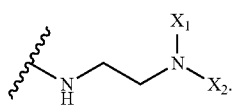

In some embodiments, $A_1$ is alkanediyl$_{(C \leq 12)}$. In some embodiments, $A_1$ is —CH$_2$— or —CH$_2$CH$_2$—. In some embodiments, $A_2$ is alkanediyl$_{(C \leq 12)}$. In some embodiments, $A_2$ is —CH$_2$— or —CH$_2$CH$_2$—. In some embodiments, $A_3$ is alkanediyl$_{(C \leq 12)}$. In some embodiments, $A_3$ is —CH$_2$— or —CH$_2$CH$_2$—. In some embodiments, $A_4$ is alkanediyl$_{(C \leq 12)}$. In some embodiments, $A_4$ is —CH$_2$— or —CH$_2$CH$_2$—. In some embodiments, $R_1$ is hydroxy. In some embodiments, $R_2$ is

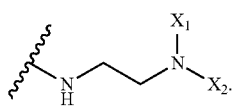

In some embodiments, $R_3$ is

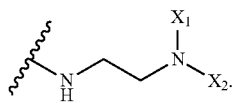

In some embodiments, $R_4$ is hydroxy. In some embodiments, $n_1$ is 1. In other embodiments, $n_1$ is 2. In some embodiments, $n_2$ is 1. In other embodiments, $n_2$ is 2. In some embodiments, $n_3$ is 1. In other embodiments, $n_3$ is 2. In some embodiments, $n_4$ is 1. In other embodiments, $n_4$ is 2. In some embodiments, $x_1$ is 1. In other embodiments, $x_1$ is 2. In some embodiments, $x_2$ is 1. In other embodiments, $x_2$ is 2. In some embodiments, $x_3$ is 1. In other embodiments, $x_3$ is 2. In some embodiments, $x_4$ is 1. In other embodiments, $x_4$ is 2. In some embodiments, $X_1$ is heteroaralkyl$_{(C \leq 12)}$. In some embodiments, $X_1$ is 2-pyridinylmethyl. In other embodiments, $X_1$ is 2-(2-pyridinyl)ethyl. In some embodiments, $X_2$ is heteroaralkyl$_{(C \leq 12)}$. In some embodiments, $X_2$ is 2-pyridinylmethyl. In other embodiments, $X_2$ is 2-(2-pyridinyl)ethyl. In some embodiments, the compound is a metal complex and further comprises a metal ion chelated as defined by the formula:

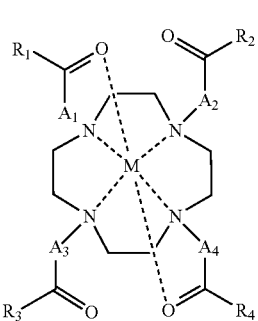

(IV)

wherein: $A_1$, $A_2$, $A_3$, $A_4$, $R_1$, $R_2$, $R_3$, $R_4$ are as defined above; and M is a metal ion; or a deprotonated form or a salt thereof. In some embodiments, M is Mn$^{2+}$, Mn$^{3+}$, or a lanthanide ion. In some embodiments, M is Gd$^{3+}$, Eu$^{3+}$, Dy$^{3+}$, or Tb$^{3+}$. In some embodiments, M is Gd$^{3+}$. In some embodiments, the compound is further defined as:

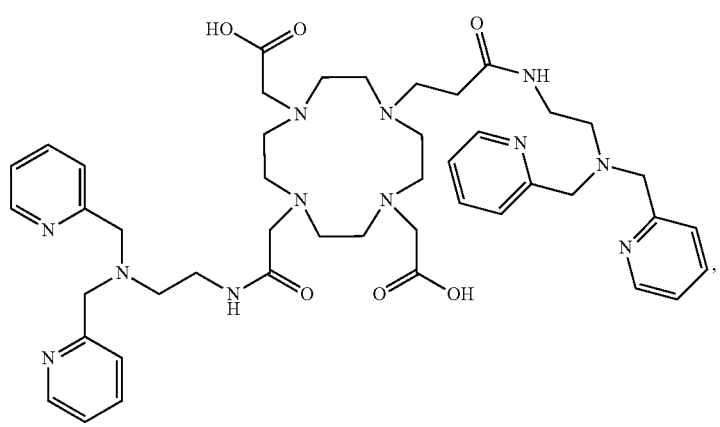

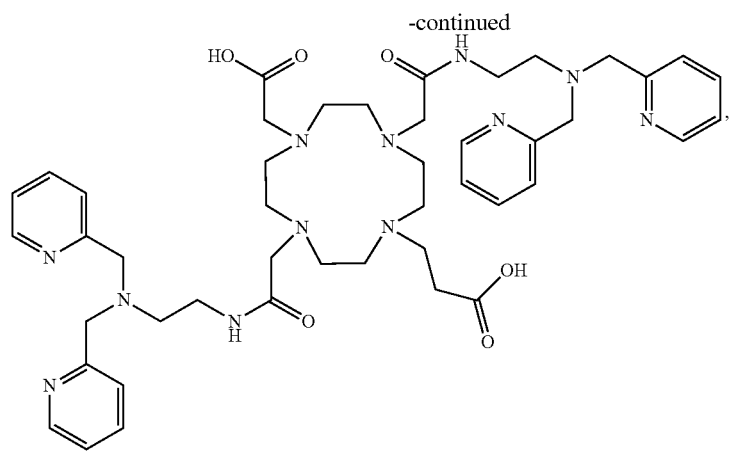
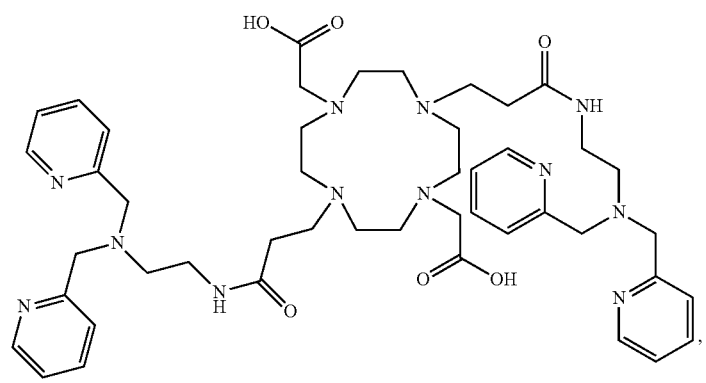
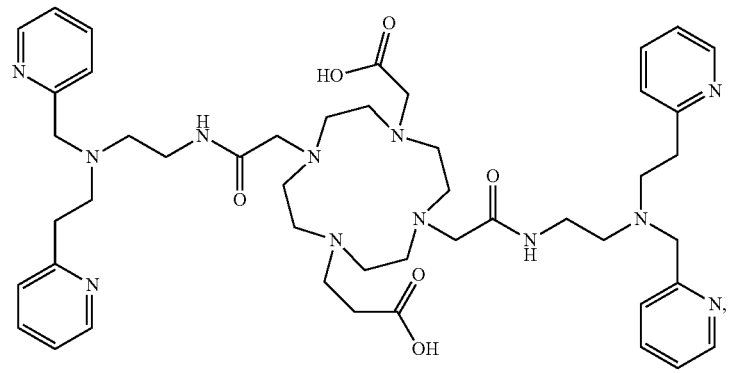
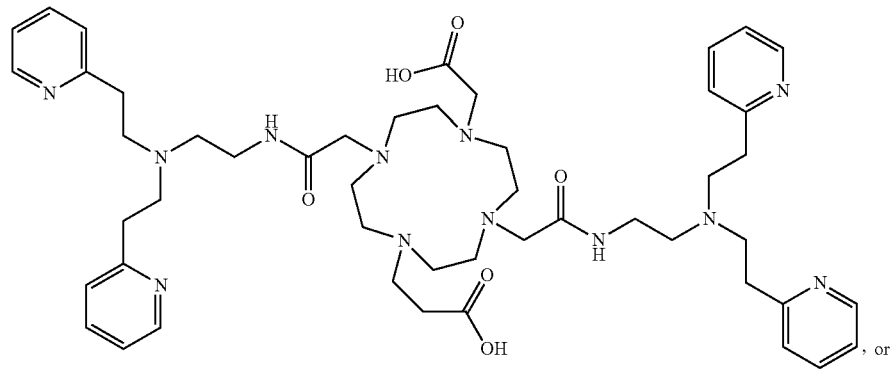

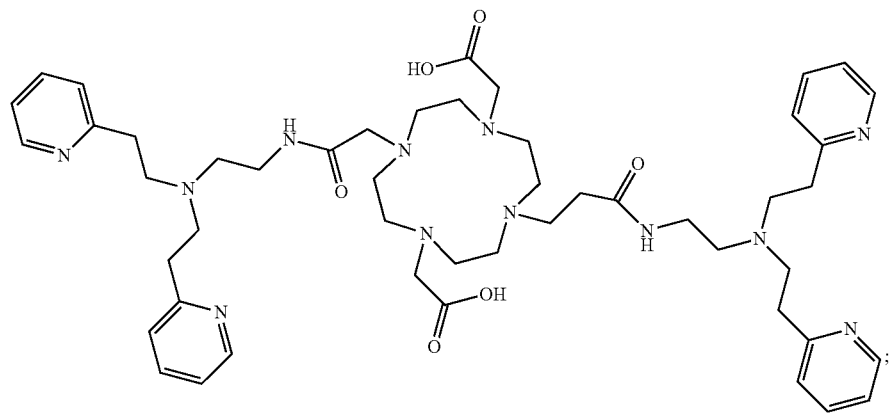
or a metal complex, a deprotonated form or a salt thereof. In some embodiments, the compound is further defined as a metal complex of the formula:
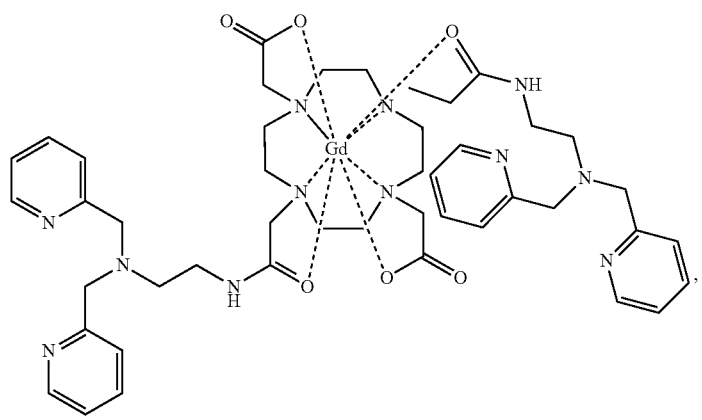
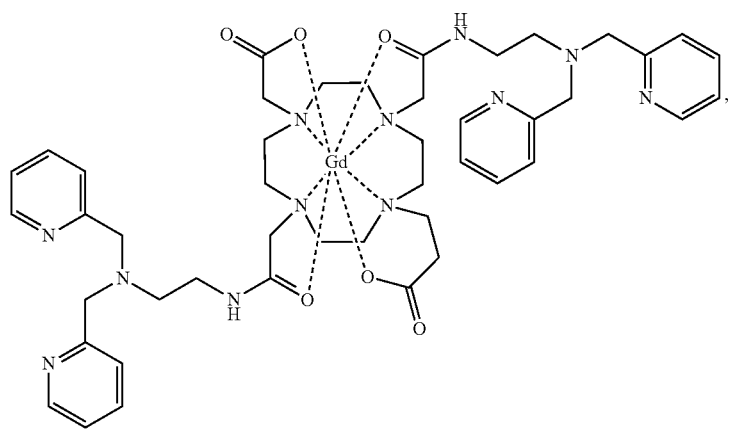

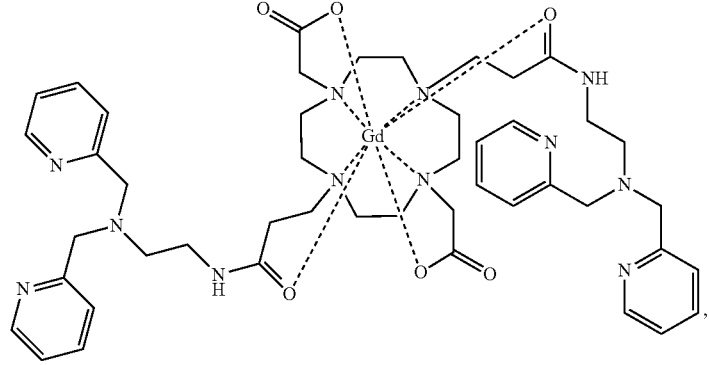
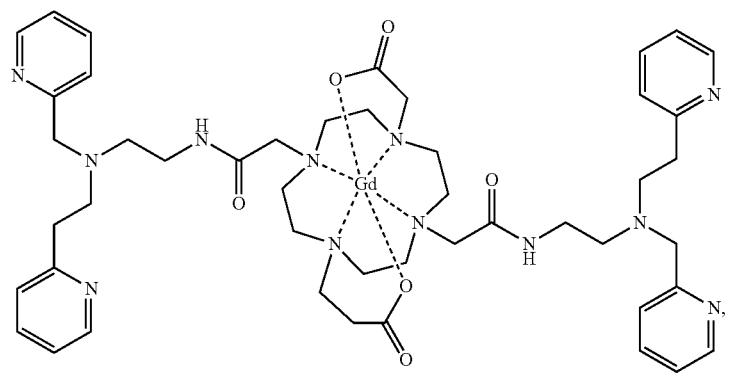
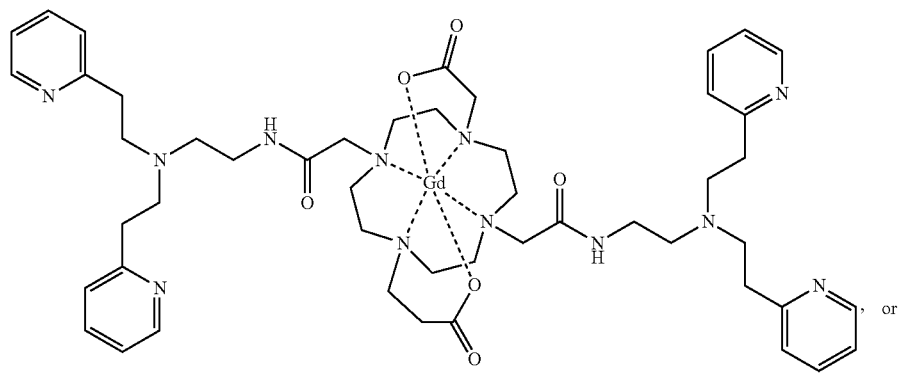, or
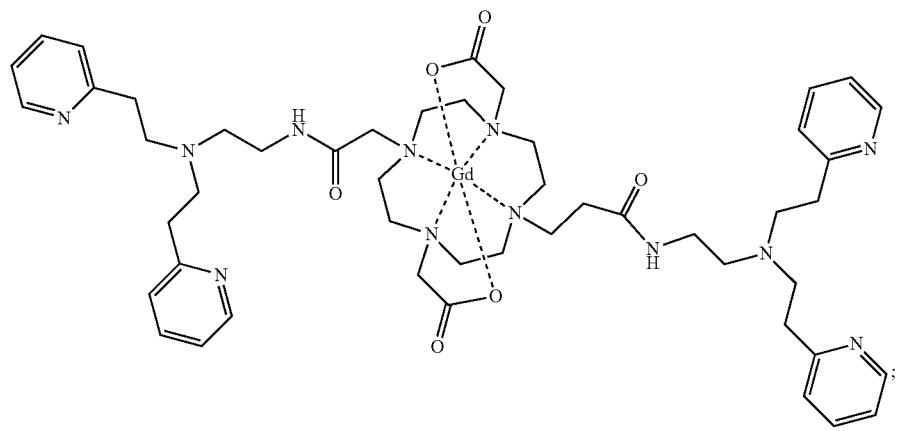

or a deprotonated form or a salt thereof.

In another aspect, the present disclosure provides a pharmaceutical composition comprising a compound of the present disclosure and a pharmaceutically acceptable carrier. In some embodiments, the composition is formulated for administration orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctival, subcutaneously, sublingually, topically, transbuccally, transdermally, vaginally, in cremes, in lipid compositions, via a catheter, via a lavage, via continuous infusion, via infusion, via inhalation, via injection, via local delivery, or via localized perfusion. In some embodiments, the pharmaceutical composition is formulated as a unit dose form in an amount sufficient to image a patient when administered thereto.

In yet another aspect, the present disclosure provides a method of imaging a patient comprising the steps of a) administering to the patient a compound or composition of the present disclosure; and b) obtaining an imaging scan of the patient. In some embodiments, the method comprises detecting the presence of $Zn^{2+}$ ions in tissue. In some embodiments, the collected imaging scan is from an MRI. In some embodiments, the method further comprises analyzing the imaging scan comprising identifying changes in $Zn^{2+}$ concentration. In some embodiments, the imaging is performed in vivo. In some embodiments, analyzing the imaging scan produces a diagnosis of a disease. In some embodiments, the disease is diabetes mellitus or cancer. In some embodiments, the cancer is prostate cancer. In some embodiments, the patient is a mammal. In some embodiments, the patient is a human.

In still another aspect, the present disclosure provides a method of imaging the pancreas in vivo in a patient to determine the onset of β-cell degeneration comprising the steps of: a) administering to the patient a compound or composition of the present disclosure; b) obtaining an imaging scan of the patient; and c) determining the presence of $Zn^{2+}$ ions. In some embodiments, the imaging scan is from an MRI. In some embodiments, the method further comprises determining the concentration of $Zn^{2+}$ ions. In some embodiments, the method further comprises administering insulin to the patient before collecting the imaging scan. In some embodiments, the onset of β-cell degeneration indicates the onset of diabetes mellitus. In some embodiments, the patient is a human.

In yet another aspect, the present disclosure provides a method of imaging the prostate in vivo in a patient to determine the presence of a prostate tumor comprising the steps of: a) administering to the patient a compound or composition of the present disclosure; b) obtaining an imaging scan of the patient; and c) determining the presence of $Zn^{2+}$ ions. In some embodiments, the imaging scan is from an MRI. In some embodiments, the method further comprises determining the concentration of $Zn^{2+}$ ions. In some embodiments, lower concentration of $Zn^{2+}$ ions indicates the presence of a prostate tumor. In some embodiments, the prostate tumor is a malignant prostate tumor. In some embodiments, the patient is a human.

In still another aspect, the present disclosure provides a method of preparing an imaging agent comprising reacting a ligand of the formula:

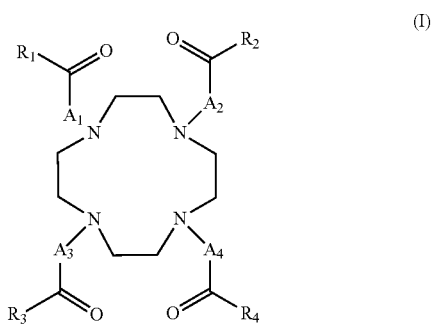

(I)

wherein: $A_1$, $A_2$, $A_3$, and $A_4$ are each independently alkanediyl$_{(C \leq 12)}$ or substituted alkanediyl$_{(C \leq 12)}$; and $R_1$, $R_2$, $R_3$, and $R_4$ are each independently hydroxy, amino, alkylamino$_{(C \leq 12)}$, substituted alkylamino$_{(C \leq 12)}$, dialkylamino$_{(C \leq 12)}$, substituted dialkylamino$_{(C \leq 12)}$, or

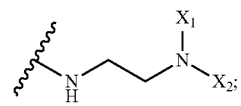

wherein: $X_1$ and $X_2$ are each independently heteroaralkyl$_{(C \leq 12)}$ or substituted heteroaralkyl$_{(C \leq 12)}$; provided that at least one of $A_1$, $A_2$, $A_3$, or $A_4$ is not —$CH_2$— with a metal salt in a solvent to form a compound of the formula:

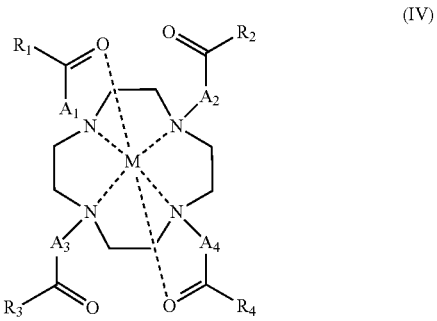

(IV)

wherein: $A_1$, $A_2$, $A_3$, $A_4$, $R_1$, $R_2$, $R_3$, $R_4$ are as defined above; and M is a metal ion; or a salt or deprotonated form thereof. In some embodiments, the method further comprises a solvent. In some embodiments, the solvent is an organic solvent. In some embodiments, the solvent is acetonitrile. In some embodiments, the solvent is water. In some embodiments, the method further comprises adding an acid or base. In some embodiments, the method further comprises adding an acid. In some embodiments, the acid is hydrochloric acid. In other embodiments, the method further comprises adding a base. In some embodiments, the base is sodium hydroxide. In some embodiments, the metal salt is a gadolinium salt. In some embodiments, the metal salt is $GdCl_3$. In some embodiments, the metal salt is $GdCl_3 \cdot 6H_2O$.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

DESCRIPTION OF ILLUSTRATIVE EMBODIMENTS

Figure 1:
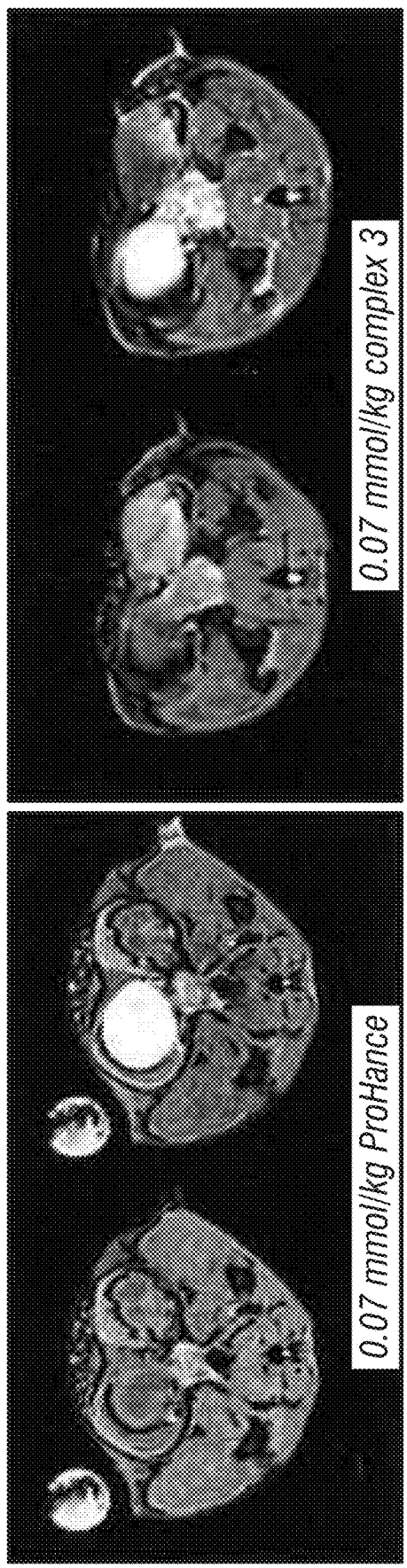
FIG. 1 shows the $T_1$-weighted MR images (9.4T, ge3D pulse sequence) of prostatic tissue in C57bl mice using ProHance (left) and compound 3 (right).
Figure 2:
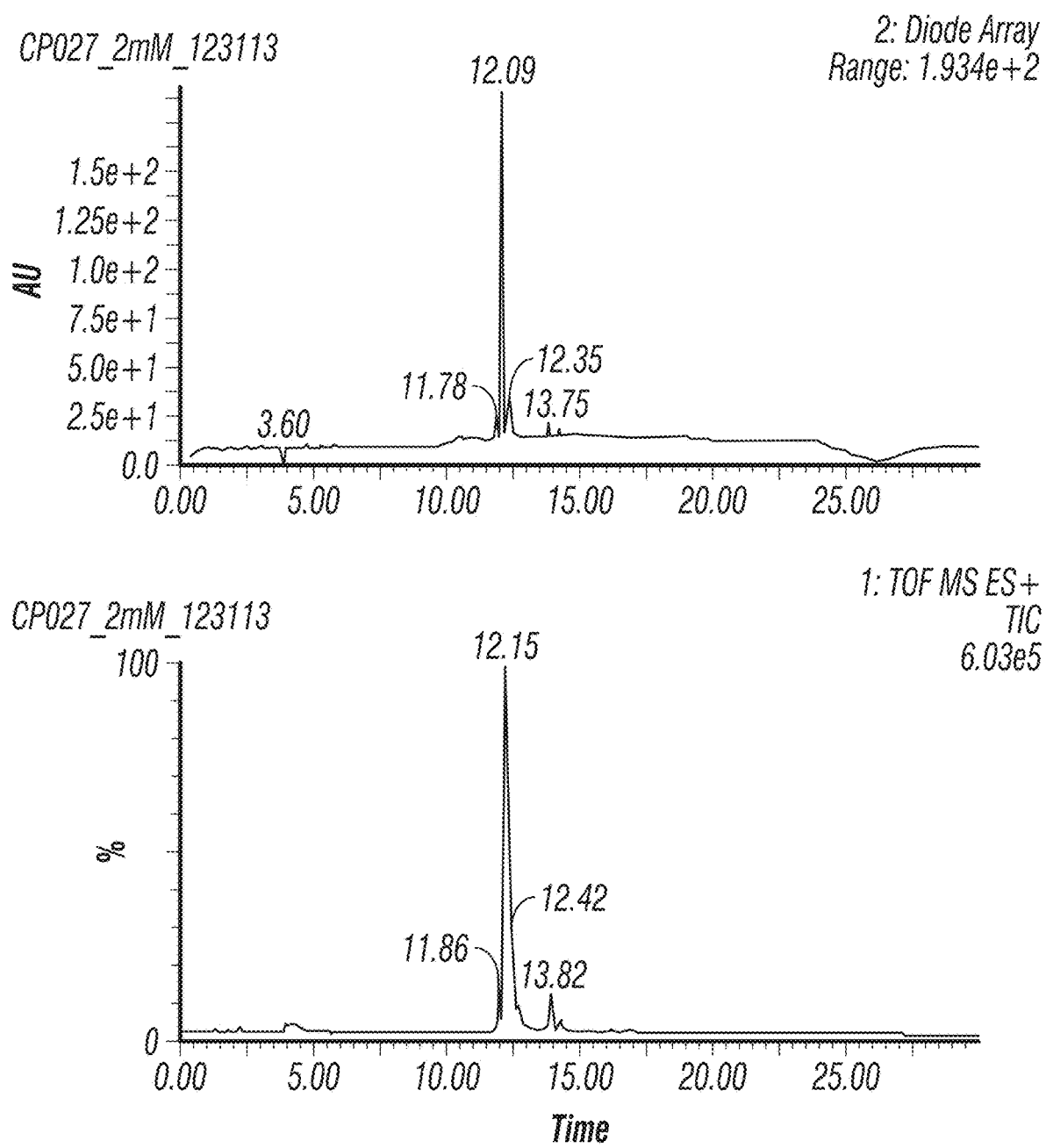
FIG. 2 shows the HPLC trace and mass spectra for Complex 3.
Figure 2:
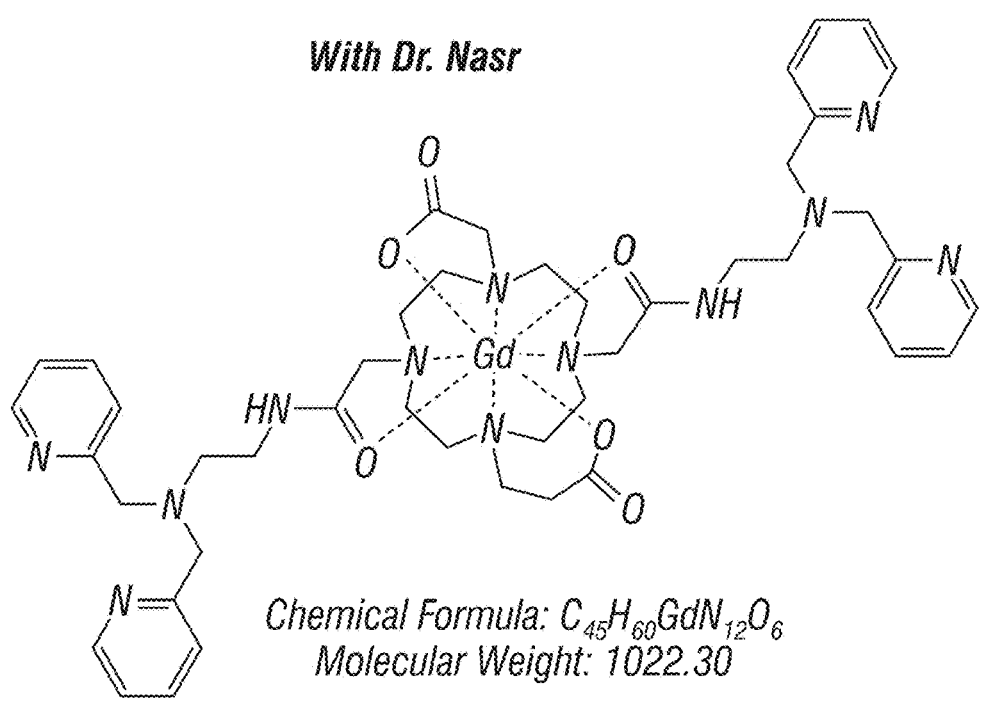
Figure 2:
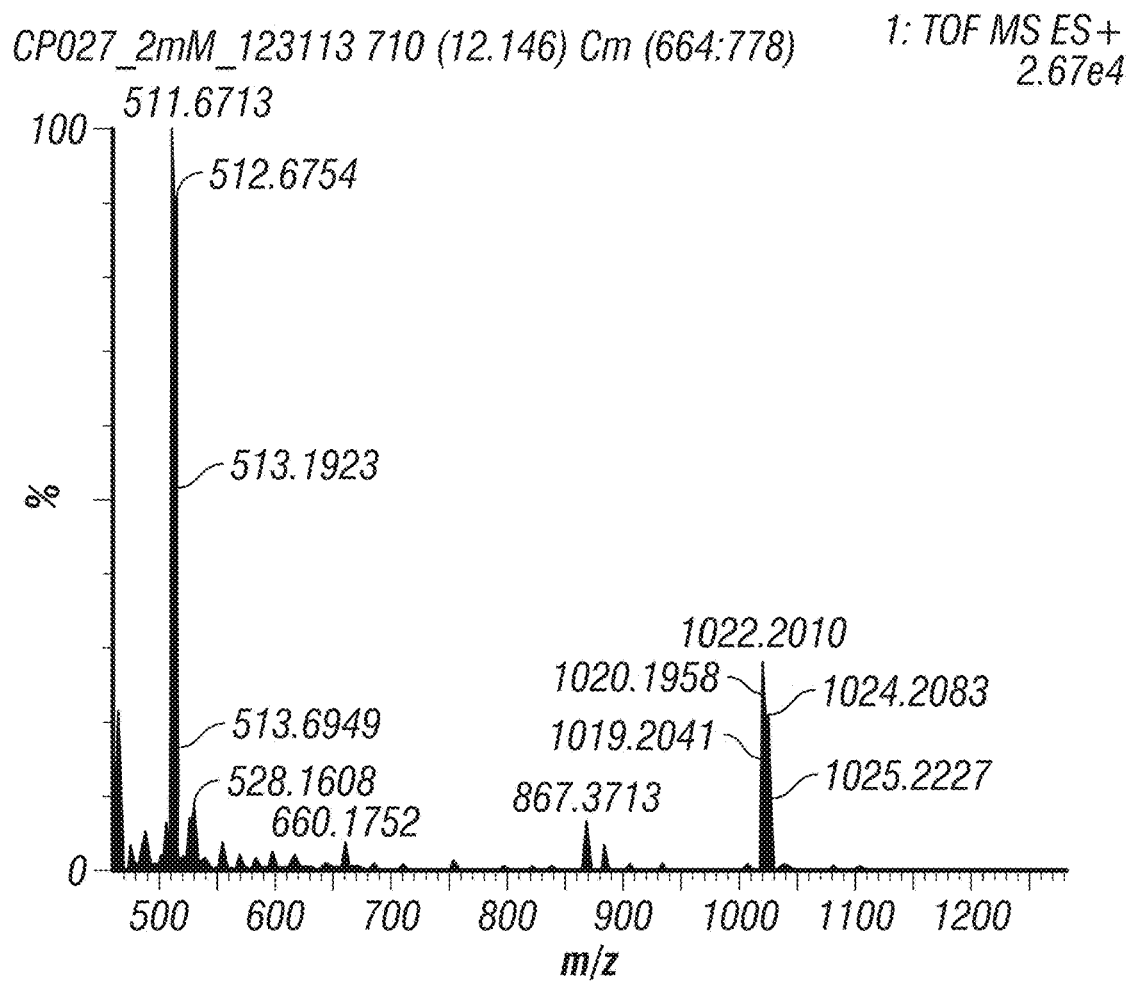
Figure 3:
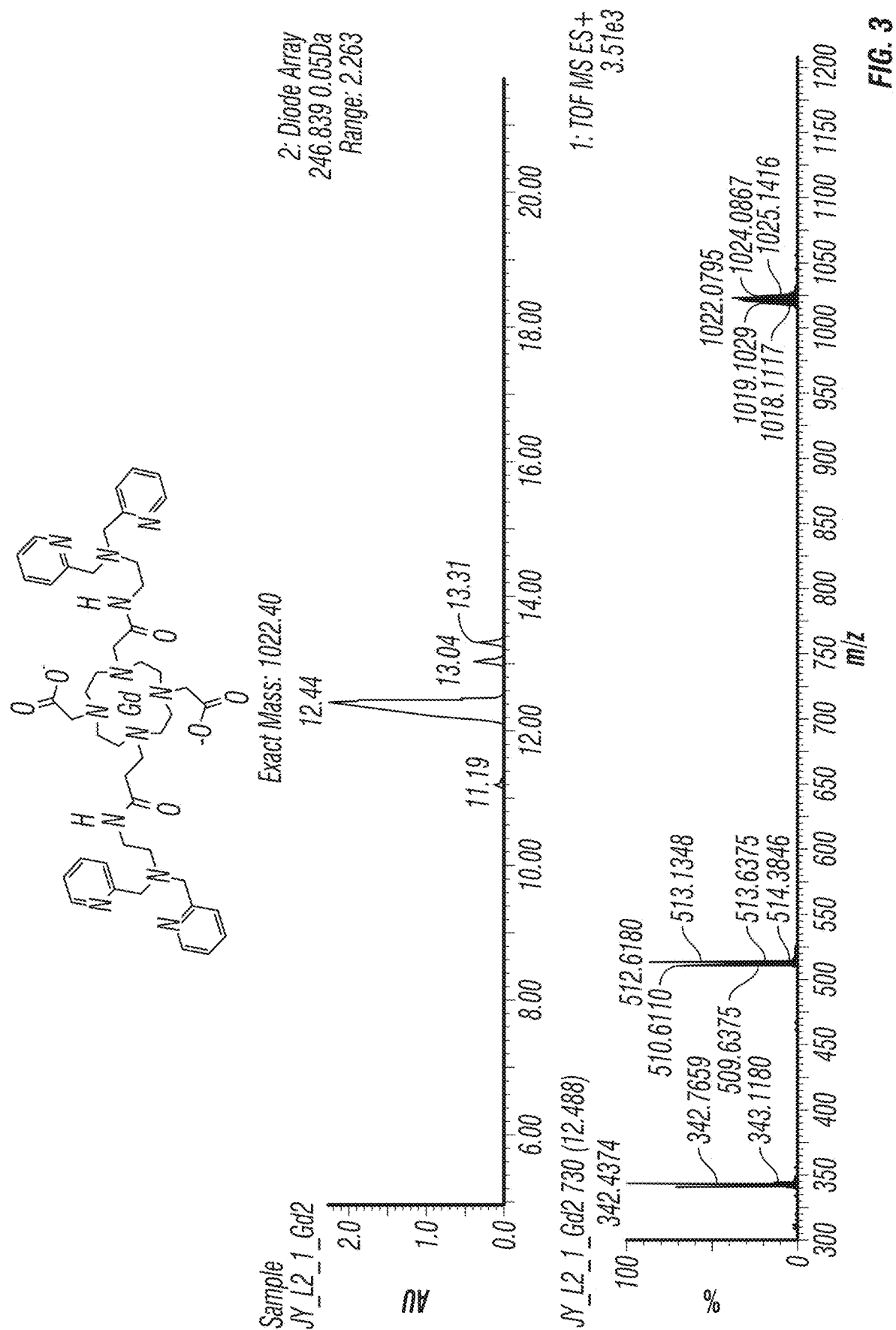
FIG. 3 shows the HPLC trace and mass spectra for Complex 2.
Figure 4:
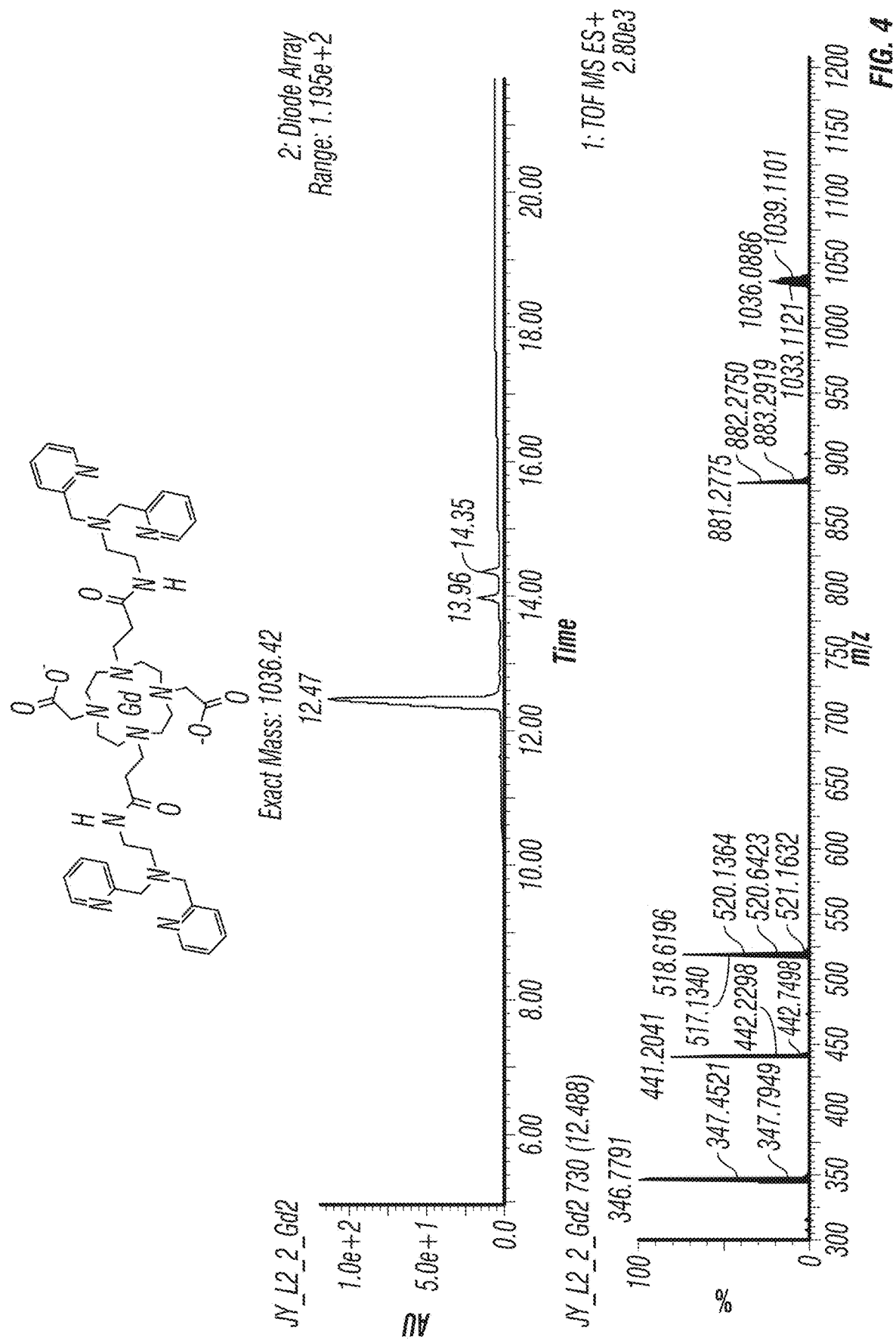
FIG. 4 shows the HPLC trace and mass spectra for Complex 4.
Figure 5:
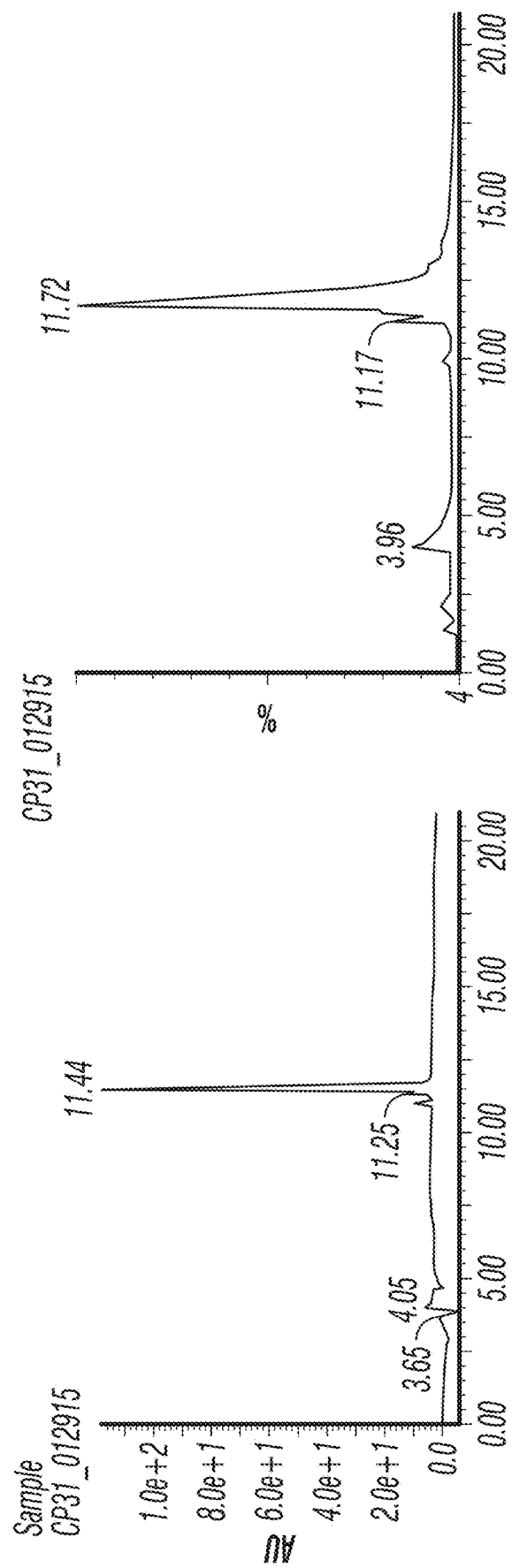
FIG. 5 shows the HPLC trace and mass spectra for Complex 5.
Figure 5:
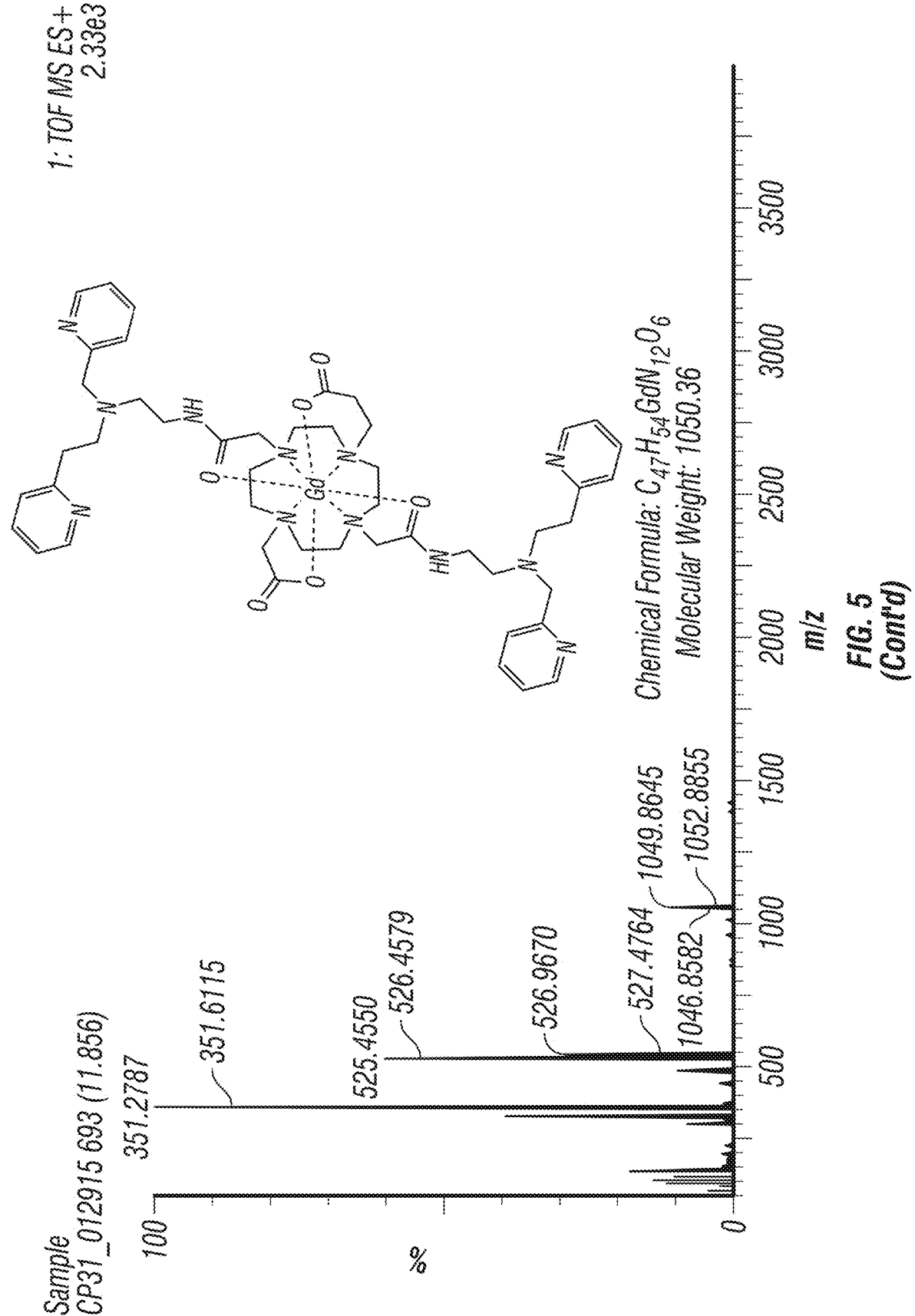
Figure 6:
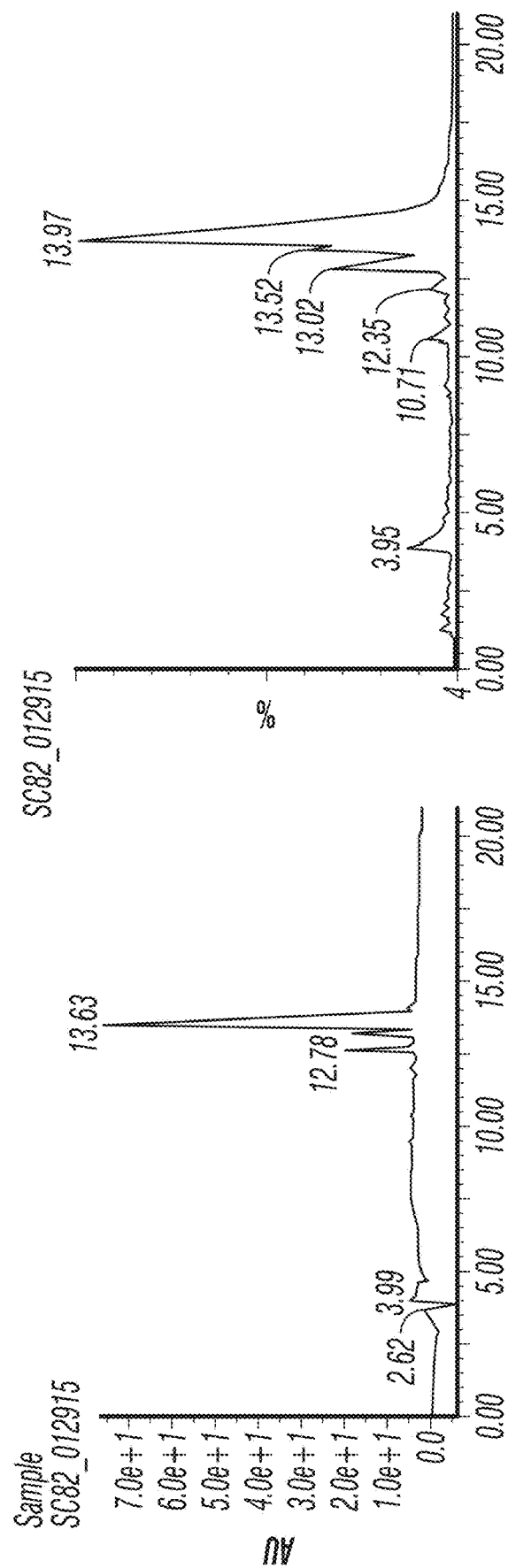
FIG. 6 shows the HPLC trace and mass spectra for Complex 6.
Figure 6:
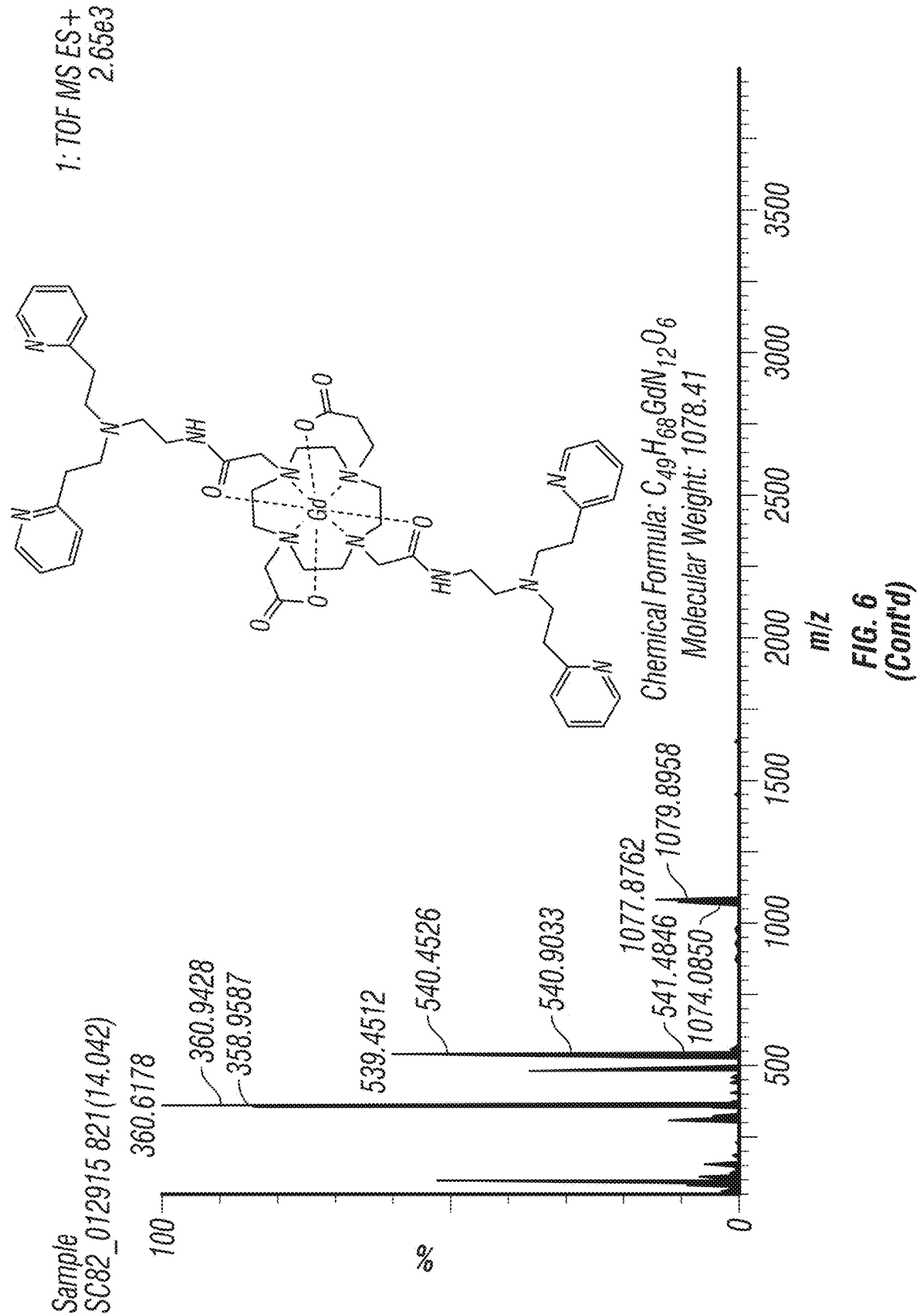
Figure 7:
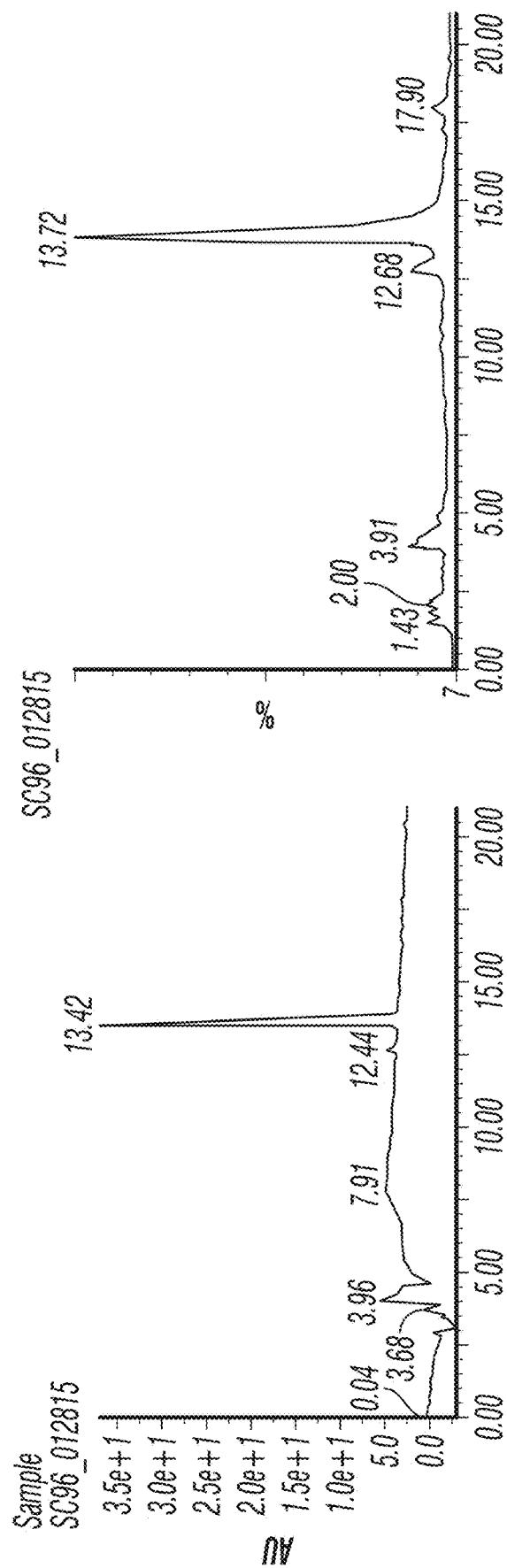
FIG. 7 shows the HPLC trace and mass spectra for Complex 7.
Figure 7:
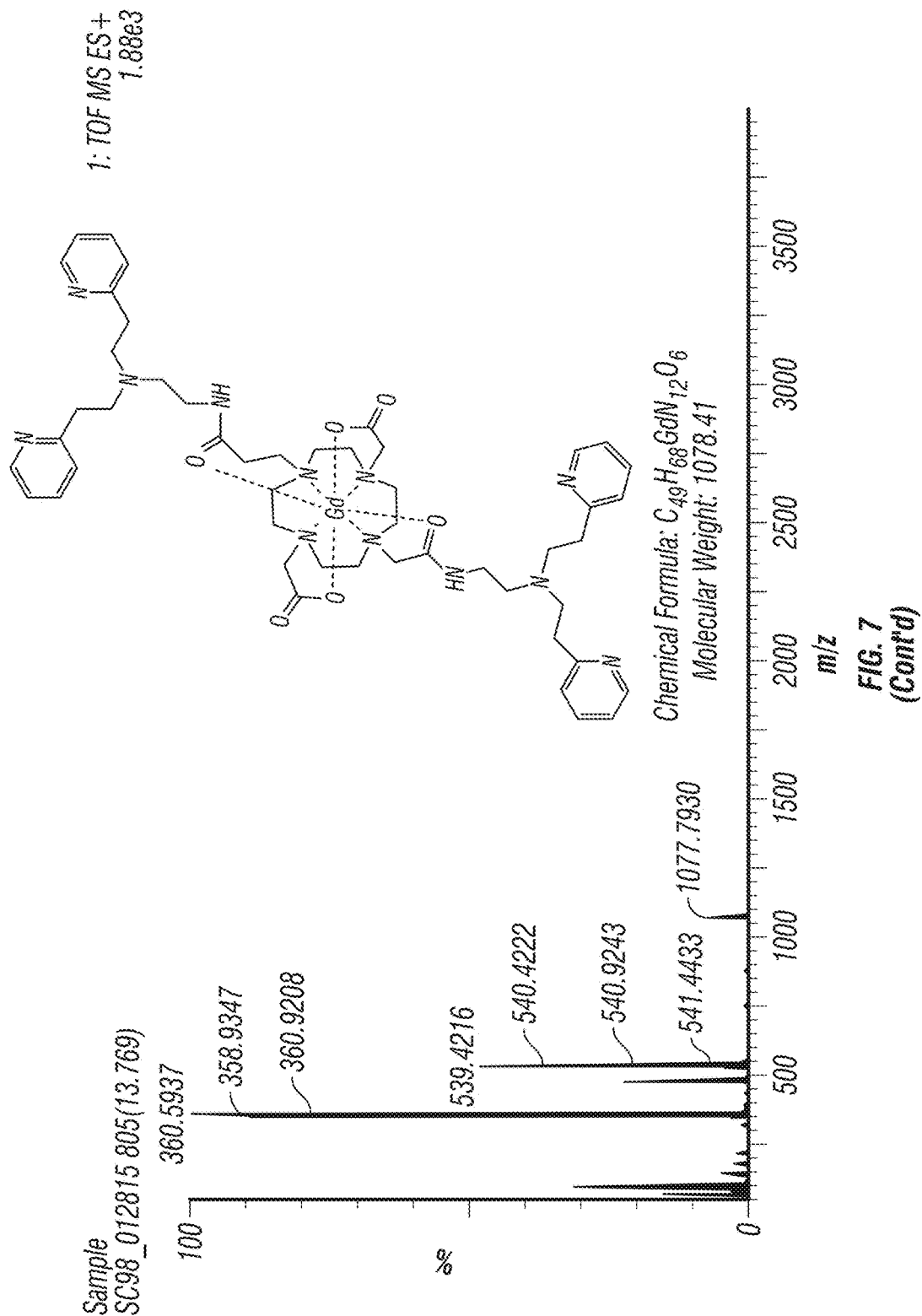

In some aspects, the present disclosure provides contrast agents containing a central gadolinium(III) 1,4,7,10-tetraazacyclododecane-1,4,7,10-tetraacetic acid (DOTA) moiety and two zinc(II) binding units, namely di-2-picolylamine, that are linked to this moiety. Upon complexation with two zinc(II) ions, the agent has been demonstrated to bind to serum albumin. This particular binding motif may be used to limit the molecular rotation of the agent in some embodiments, thereby increases its relaxivity that in turn leads to a better contrast ratio. This particular binding motif may be used to increase the water exchange rate on the central gadolinium(III) metal core. In some embodiments, the water exchange rate is increased by an increase of hydrophobic interactions within the coordination sphere around gadolinium(III). Without being bound by theory, an increase in water exchange translates into a significantly increased $r_1$ relaxivity, i.e. the ability of magnetic compounds to increase the relaxation rates of surrounding water proton spins. Additionally, in some embodiments, the present disclosure has a higher $T_1$ relaxivity so that it can be detected effectively at a much lower concentration (µM) than contrast agents of the present disclosure. Furthermore, in some embodiments, a lower concentration of the contrast agent which possesses a higher potency can be used to image small biological targets. Finally, in some embodiments, the contrast agent has additional advantages in terms of toxicity and adverse effects associated with the compound class. In some embodiments, compounds of the disclosure also have the advantage that they are more efficacious than, less toxic than, longer acting than, more potent than, produce fewer side effects than, more easily absorbed and/or have a better pharmacokinetic profile (e.g., higher oral bioavailability and/or lower clearance) than, and/or have other useful pharmacological, physical, or chemical properties over, known compounds, whether for use in the indications stated herein or otherwise.

A. DEFINITIONS

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; and "sulfinyl" means —S(O)—.

In the context of chemical formulas, the symbol "—" means a single bond, "=" means a double bond, and "≡" means triple bond. The symbol "----" represents an optional bond, which if present is either single or double or may represent a dative or coordination bond to a metal atom. The symbol "═" represents a single bond or a double bond. Thus, for example, the formula

includes

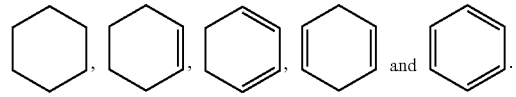

And it is understood that no one such ring atom forms part of more than one double bond. Furthermore, it is noted that the covalent bond symbol "—", when connecting one or two stereogenic atoms, does not indicate any preferred stereochemistry. Instead, it cover all stereoisomers as well as mixtures thereof. The symbol "⌇", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◄" means a single bond where the group attached to the thick end of the wedge is "out of the page." The symbol "⫽" means a single bond where the group attached to the thick end of the wedge is "into the page". The symbol "⌇" means a single bond where the geometry around a double bond (e.g., either E or Z) is undefined. Both options, as well as combinations thereof are therefore intended. The bond orders described above are not limiting when one of the atoms connected by the bond is a metal atom (M). In such cases, it is understood that the actual bonding may comprise significant multiple bonding and/or ionic character. Therefore, unless indicated otherwise, the formulas M-C, M=C, M----C, and M≡C, each refers to a bond of any and type and order between a metal atom and a carbon atom. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

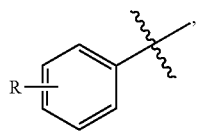

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

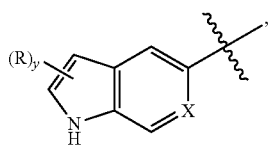

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms. (Cn-n') defines both the minimum (n) and maximum number (n') of carbon atoms in the group. Similarly, "alkyl$_{(C2-10)}$" designates those alkyl groups having from 2 to 10 carbon atoms.

The term "saturated" as used herein means the compound or group so modified has no carbon-carbon double and no carbon-carbon triple bonds, except as noted below. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl).

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl, with the carbon atom that forms the point of attachment also being a member of one or more non-aromatic ring structures wherein the cycloalkyl group consists of no atoms other than carbon and hydrogen. As used herein, the term does not preclude the presence of one or more alkyl groups (carbon number limitation permitting) attached to the ring or ring system. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or tBu), —CH$_2$C(CH$_3$)$_3$ (neo-pentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and

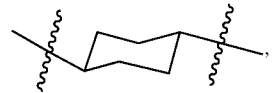 [SMILES: *C1CCC(*)CC1]

are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH$_2$, =CH(CH$_2$CH$_3$), and =C(CH$_3$)$_2$. An "alkane" refers to the compound H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH₂OC(O)CH₃, —CH₂NH₂, —CH₂N(CH₃)₂, and —CH₂CH₂Cl. The term "haloalkyl" is a subset of substituted alkyl, in which one or more hydrogen atoms has been substituted with a halo group and no other atoms aside from carbon, hydrogen and halogen are present. The group, —CH₂Cl is a non-limiting example of a haloalkyl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl, aryl, and/or aralkyl groups (carbon number limitation permitting) attached to the aromatic ring or aromatic ring system. Non-limiting examples of heteroarenediyl groups include:

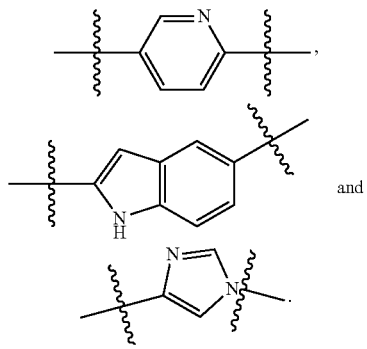

and

A "heteroarene" refers to the compound H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂.

The term "heteroaralkyl" when used without the "substituted" modifier refers to the monovalent group -alkanediyl-heteroaryl, in which the terms alkanediyl and aryl are each used in a manner consistent with the definitions provided above. Non-limiting examples of heteroaralkyls are: 2-pyridinylmethyl and 2-imidazolyl-ethyl. When the term heteroaralkyl is used with the "substituted" modifier one or more hydrogen atom from the alkanediyl and/or the heteroaryl group has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂. Non-limiting examples of substituted heteroaralkyls are: (3-hydroxypyridinyl)-methyl, and 3-chloro-2-thiazolylethyl.

The term "metal complex" is a compound comprising at least one compound which can act as a ligand (i.e. contains at least one pair of electrons, a charge, or an empty orbital) and at least one metal ion, wherein the ligand and the metal ion are attached to one another by one or more metal-ligand bonds.

The term "deprotonated form" is a compound in which one or more acidic hydrogen atoms have been removed to from an anion. In some embodiments, an acidic hydrogen has a pK$_a$ less than 20. In a preferred embodiments, the pK$_a$ is less than 10. In a more preferred embodiment, the pK$_a$ is less than 7.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, horse, sheep, goat, dog, cat, mouse, rat, guinea pig, or transgenic species thereof. In certain embodiments, the patient or subject is a primate. Non-limiting examples of human subjects are adults, juveniles, infants and fetuses.

"Pharmaceutically acceptable salts" means salts of compounds of the present disclosure which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this disclosure is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed 2n, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

The above definitions supersede any conflicting definition in any of the reference that is incorporated by reference herein. The fact that certain terms are defined, however, should not be considered as indicative that any term that is undefined is indefinite. Rather, all terms used are believed to describe the disclosure in terms such that one of ordinary skill can appreciate the scope and practice the present disclosure.

B. COMPOUNDS

In some aspects, the present disclosure provides novel ligands of the formula:

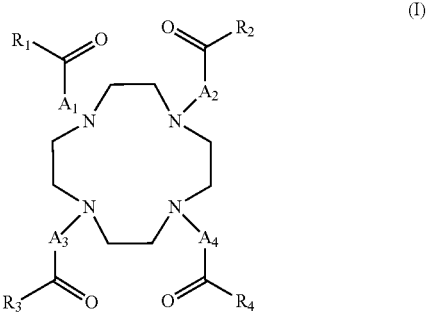

wherein: $A_1$, $A_2$, $A_3$, and $A_4$ are each independently alkanediyl$_{(C \leq 12)}$ or substituted alkanediyl$_{(C \leq 12)}$; and $R_1$, $R_2$, $R_3$, and $R_4$ are each independently hydroxy, amino, alkylamino$_{(C \leq 12)}$, substituted alkylamino$_{(C \leq 12)}$, dialkylamino$_{(C \leq 12)}$, substituted dialkylamino$_{(C \leq 12)}$, or

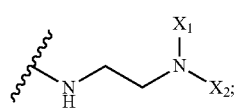

wherein: $X_1$ and $X_2$ are each independently heteroaralkyl$_{(C \leq 12)}$ or substituted heteroaralkyl$_{(C \leq 12)}$; provided that at least one of $A_1$, $A_2$, $A_3$, or $A_4$ is not —CH$_2$—; or a metal complex, a deprotonated form, or a salt thereof. Additionally, the present disclosure may relate to a metal complex of the formula:

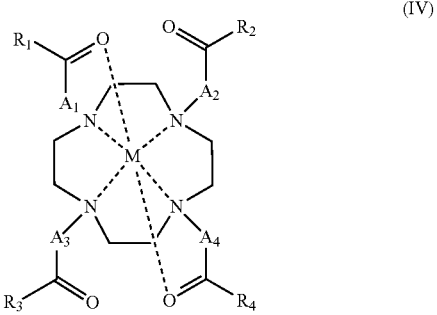

wherein: $A_1$, $A_2$, $A_3$, $A_4$, $R_1$, $R_2$, $R_3$, $R_4$ are as defined above; and M is a metal ion; or a deprotonated form or a salt thereof.

In some embodiments, the compounds of the present disclosure are included in Table 1. These compounds may also be referred to as complexes throughout the application.
TABLE 1
Compounds of the Present Disclosure
| Compound Number | Compound |
|---|---|
| Complex 2 | 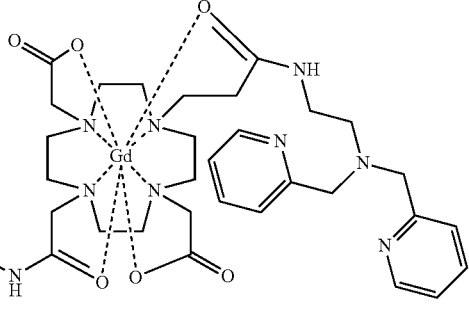 |
| Complex 3 | 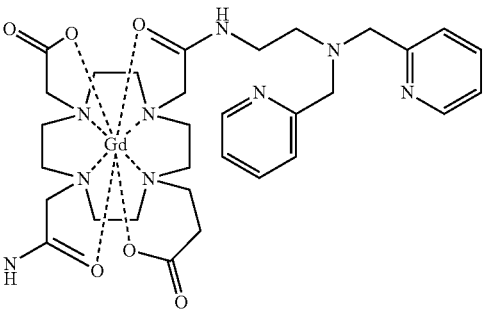 |
| Complex 4 | 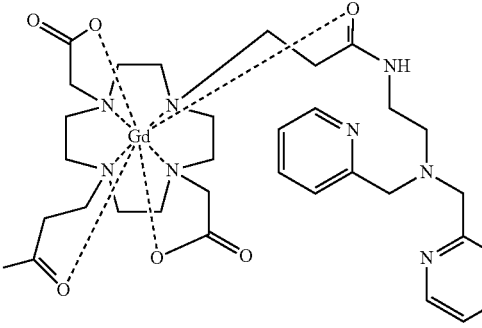 |

US 11,097,017 B2

23

TABLE 1-continued

Compounds of the Present Disclosure

| Compound Number | Compound |
|---|---|
| Complex 5 | 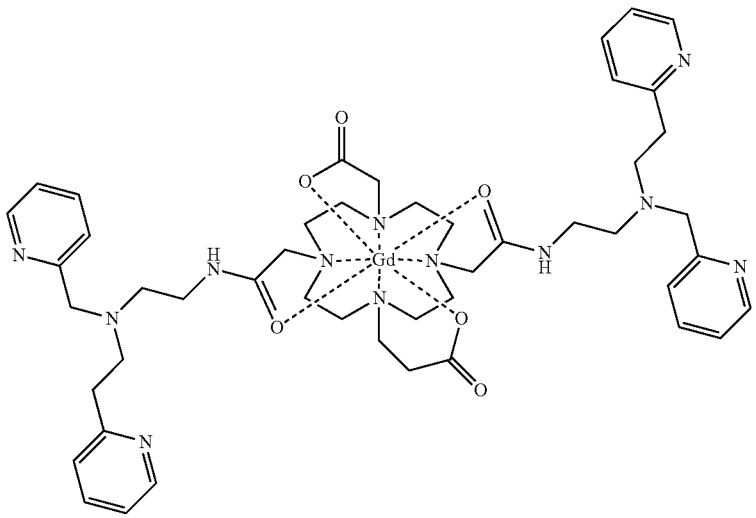 |
| Complex 6 | 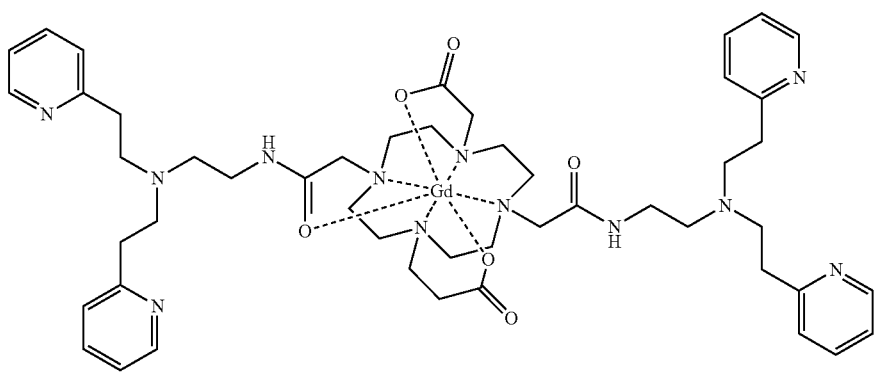 |
| Complex 7 | 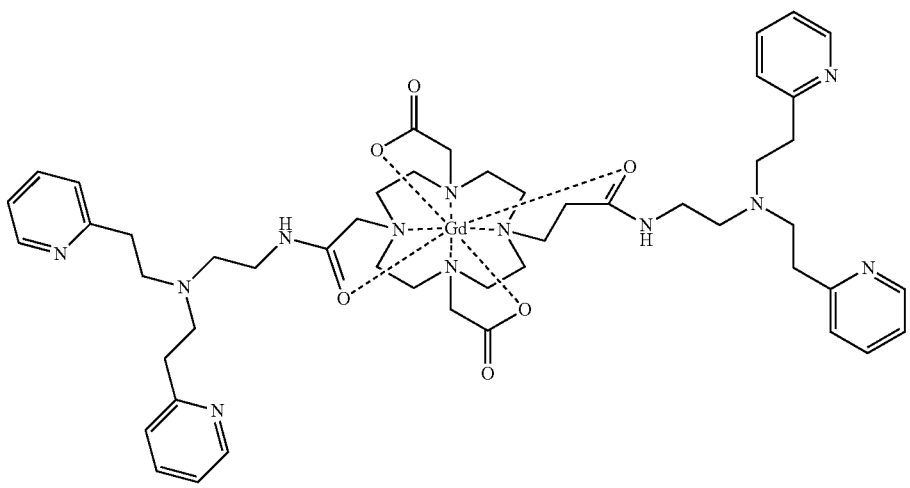 |

The novel compounds, complexes, and ligands provided herein, may be prepared according to the methods described below. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

The ligands described in this disclosure may contain one or more asymmetrically-substituted carbon or nitrogen atoms, and may be isolated in optically active or racemic form. Thus, all chiral, diastereomeric, racemic form, epimeric form, and all geometric isomeric forms of a structure are intended, unless the specific stereochemistry or isomeric form is specifically indicated. The ligands of this disclosure may occur as racemates and racemic mixtures, single enantiomers, diastereomeric mixtures and individual diastereomers. In some embodiments, a single diastereomer is obtained. The chiral centers of the present disclosure can have the S or the R configuration.

In addition, atoms making up the ligands of the present disclosure are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$. Similarly, it is contemplated that one or more carbon atom(s) of a compound of the present disclosure may be replaced by a silicon atom(s). Furthermore, it is contemplated that one or more oxygen atom(s) of the ligands may be replaced by a sulfur or selenium atom(s).

It should be recognized that the particular anion or cation forming a part of any salt of this disclosure is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

C. PREPARATION OF LIGAND AND IMAGING CHARACTERIZATION

1. Synthesis

In some embodiments, the present ligand can be prepared by selectively protected the amine groups of the DOTA to allow for the introduction of a unique group to each of the linkers. In some embodiments, this modification is carried out using orthogonally protected bifunctional linkers containing a carboxylate group and a leaving group such as a halogen. In some embodiments, this reaction is carried out using a standard nucleophilic displacement. The orthogonally protected carboxylate can then be deprotected and coupled to additional functional groups though standard amide bond forming methodologies.

Furthermore, the complex can be metalated before, during, or after the synthesis of the functional groups on the amines of the DOTA macrocycle provided that the synthetic methods are not negatively affect by the presence of the metal ion. In some embodiments, the metal ion is introduced into the DOTA compound after the introduction of the functional groups to the amines of the DOTA macrocycle.

2. Relaxometric Studies

In some embodiments, MRI contrast agents are typically characterized by a $T_1$ proton relaxivity value. The relaxivity of low molecular weight Gd-ligand complex that has rapid water exchange kinetics may be dominated by the inner-sphere contribution. Without being bound by theory, the Solomon-Bloembergen-Morgan (SBM) theory of relaxivity predicts that inner-sphere contribution to relaxivity may be dependent on several parameters including the number of inner-sphere water molecules (q), the longitudinal relaxation time of the protons of the water molecule(s) in the inner coordination sphere, the residence time of the inner-sphere water molecule(s) and the tumbling rate of the paramagnetic complex in solution (rotational correlation time) (Caravan, et al., 1999).

3. MRI Imaging and Relaxivity Measurements

The efficacy of the probe is measured by the longitudinal relaxation rate of the water protons, which is known as relaxivity ($r_1$) (Shiraishi, et al., 2010; Huang, et al., 2011) or the measurement of other physical parameters. Without being bound by theory, according to the Bloembergen-Solomon-Morgan theory, in some embodiments, the residence lifetime of the coordinated water molecules and the rotational correlation times are factors for enhancing the relaxivities of gadolinium complexes, which are related to the intrinsic structural parameters. In some embodiments, the relaxation theory also predicts that higher relaxation rates can be obtained upon increase of the rotational correlation time of complexes. In some embodiments, small, fast tumbling molecules like Gd-DTPA show a modest decrease in $r_1$ with increasing field strength (Rohrer, et al., 2005), while big molecular weight contrast agent have high relaxivities that peak between 0.5 and 1.0 T and then sharply drop with increasing field (Rohrer, et al., 2005; Caravan, 2006).

D. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Synthetic Scheme and Experimental Procedures

Scheme 1: Synthesis of Cyclen Derivative 4 and 6
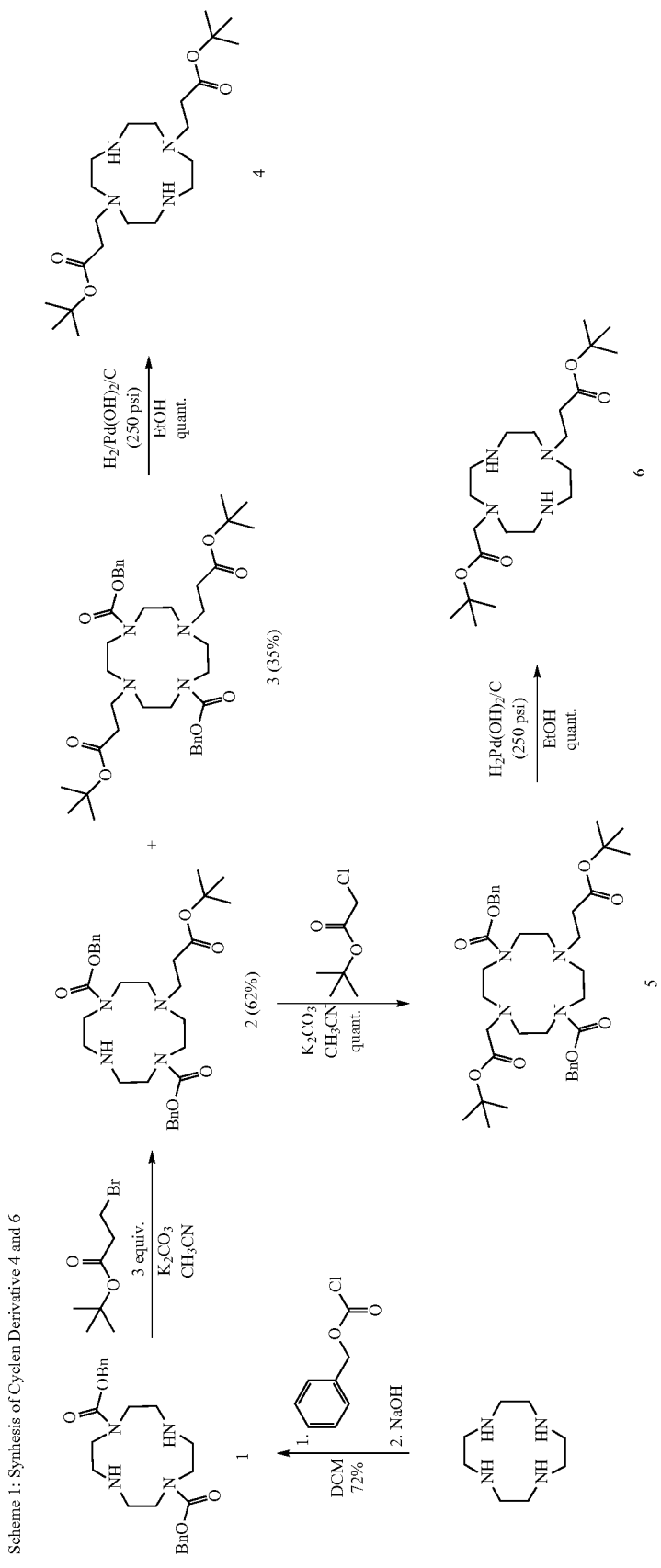

Synthesis of dibenzyl 1,4,7,10-tetraazacyclododecane-1,7-dicarboxylate (1)

1,4,7,10-tetraazacyclododecane (cyclen, 18.06 g, 105 mmol) was dissolved in 500 mL dichloromethane in a 1 L round bottom flask and cooled to 0° C. using an ice bath. Benzyl chloroformate (34 g, 200 mmol) was dissolved in 250 mL dichloromethane and added dropwise over the course of three hours while keeping the temperature at 0° C. The light yellow solution was allowed to slowly warm to room temperature and was stirred overnight. The solvent was evaporated to roughly 25% of its initial volume. 500 mL of diethyl ether were added to induce precipitation of the entire product. The white solid was filtered off using a Buchner funnel and washed with portions of diethyl ether (3×100 mL). After suspending the solid in 500 mL of water in a 2 L beaker, a sodium hydroxide solution (20%) was slowly added upon vigorous stirring until a pH of 14 was reached. The milky solution was transferred to a 100 mL separatory funnel and extracted with diethyl ether (3×200 mL). The organic layer was washed with water (3×200 mL) and dried over anhydrous sodium sulfate, filtered and evaporated in vacuo. A viscous, colorless oil was obtained. Yield: 33.30 g (75.6 mmol, 72%) $^1$H NMR (300 MHz, CDCl$_3$): δ 2.75-2.91 (m, 8H), 3.11-3.20 (m, 8H), 5.11 (s, 4H), 7.22-7.31 (m, 10H). LCMS-ESI: 441.54 (M+H)$^+$.

Synthesis of dibenzyl 4-(3-(tert-butoxy)-3-oxopropyl)-1,4,7,10-tetraazacyclododecane-1,7-dicarboxylate (2) and dibenzyl 4,10-bis(3-(tert-butoxy)-3-oxopropyl)-1,4,7,10-tetraazacyclododecane-1,7-dicarboxylate (3)

Dibenzyl 1,4,7,10-tetraazacyclododecane-1,7-dicarboxylate (1, 2.917 g, 6.62 mmol) was dissolved in 250 mL acetonitrile. Tert.butyl bromopropionate (2.769 g, 13.24 mmol) was added and the volume of the clear solution was increased to 500 mL. Potassium carbonate (1.826 g, 13.24 mmol) was added and the reaction mixture was refluxed for 16 hours at 63° C. The solvent was evaporated in vacuo. 100 mL of ethyl acetate and 100 mL water were added and the biphasic mixture was stirred for 10 minutes. The organic phase was collected using a separatory funnel, dried over anhydrous sodium sulfate, filtered and evaporated in vacuo. Column chromatography (silica, first 100% ethyl acetate to elute 3, then 90% chloroform/10% methanol to elute 2) afforded both compounds. For 2: 2.33 g (4.10 mmol, 62%); For 3: 1.61 g (2.32 mmol, 35%)

Synthesis of di-tert-butyl 3,3'-(1,4,7,10-tetraazacyclododecane-1,7-diyl)dipropionate (4)

Dibenzyl 4,10-bis(3-(tert.-butoxy)-3-oxopropyl)-1,4,7,10-tetraazacyclododecane-1,7-dicarboxylate (3, 1.0 g, 1.43 mmol) was dissolved in 50 mL ethanol. Palladium hydroxide on carbon (20%, 50 mg) were added and the reaction mixture was placed in a Parr high pressure hydrogenation vessel and allowed to react at a hydrogen pressure of 250 psi at 100° C. for 72 hours. The black reaction mixture was filtered through Celite® and the resulting colorless solution was the evaporated in vacuo to yield 4 as a colorless oil. Yield: 612.9 mg (1.43 mmol, quant.).

Synthesis of dibenzyl 4-(2-(tert-butoxy)-2-oxoethyl)-10-(3-(tert-butoxy)-3-oxopropyl)-1,4,7,10-tetraazacyclo-dodecane-1,7-dicarboxylate (5)

Dibenzyl 4-(3-(tert-butoxy)-3-oxopropyl)-1,4,7,10-tetraazacyclododecane-1,7-dicarboxylate (2, 0.735 g, 1.29 mmol) was dissolved in 25 mL acetonitrile. Tert.butyl chloroacetate (204 mg, 1.35 mmol) in 25 mL acetonitrile and potassium carbonate (0.179 mg, 1.29 mmol) were added and the reaction mixture was stirred for 48 hours at 60° C. The solvent was evaporated and the residue was redissolved in 100 mL chloroform. After washing with water (2×200 mL), the solution was dried over anhydrous sodium sulfate, filtered and evaporated in vacuo. Yield: 880.89 mg (1.29 mmol, quant.) $^1$H NMR (300 MHz, CDCl$_3$): δ 1.24 (s, 18H), 2.36 (t, 2H), 2.61-2.82 (m, 8H), 2.85-3.07 (m, 8H), 3.12 (s, 2H), 3.49 (s, 2H), 5.41 (s, 4H), 7.61-7.75 (m, 10H). LCMS-ESI: 683.86 (M+H)$^+$.

Synthesis of tert-butyl 3-(7-(2-(tert-butoxy)-2-oxoethyl)-1,4,7,10-tetraazacyclododecan-1-yl)propanoate (6)

Dibenzyl 4-(2-(tert-butoxy)-2-oxoethyl)-10-(3-(tert-butoxy)-3-oxopropyl)-1,4,7,10-tetraazacyclo-dodecane-1,7-dicarboxylate (5, 2 g, 2.93 mmol) was dissolved in 50 mL ethanol. Palladium hydroxide on carbon (20%, 100 mg) were added and the reaction mixture was placed in a Parr high pressure hydrogenation vessel and allowed to react at a hydrogen pressure of 250 psi at 100° C. for 72 hours. The black reaction mixture was filtered through Celite® and the resulting colorless solution was then evaporated in vacuo to yield 6 as a colorless oil. Yield: 1.21 g (2.93 mmol, quant.) $^1$H NMR (300 MHz, CD$_3$OD): δ 1.24 (s, 18H), 2.69 (m, 10H), 2.89 (m, 8H), 3.55 (s, 2H), 3.91 (t, 2H). LCMS-ESI: 415.60 (M+H)$^+$.

Scheme 2: Synthesis of Derivatives 8 and 10

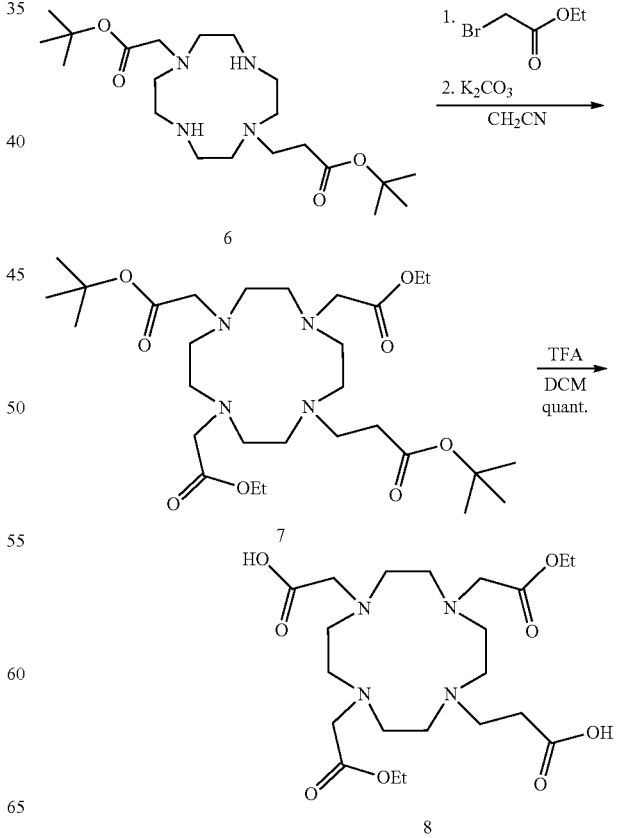

31
-continued

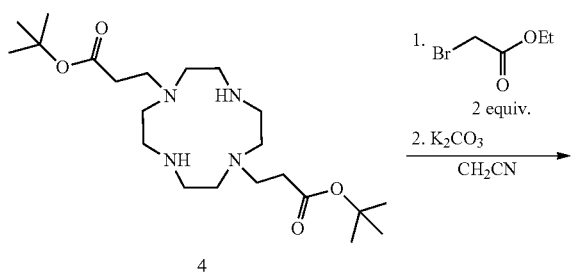

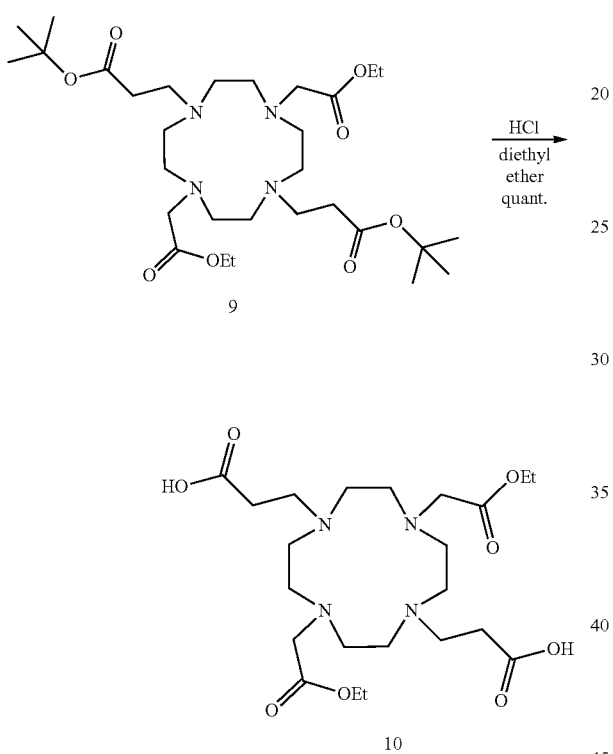

Synthesis of di-tert-butyl 3,3'-(4,10-bis(2-ethoxy-2-oxoethyl)-1,4,7,10-tetraazacyclododecane-1,7-diyl) dipropionate (9)

300 mg Compound 4 and bromo ethyl acetate (2 equiv.) were dissolved in acetonitrile. Then two equivalents of sodium bicarbonate were added and the resulting mixture was refluxed overnight. Remaining sodium bicarbonate was filtered off and the solution was concentrated in vacuo. The combined organic phase was dried over anhydrous sodium sulfate, filtered and evaporated in vacuo. Column chromatography (alumina, 95% chloroform/5% methanol to elute column) afforded pure compound 9. $^1$H NMR (400 MHz, D$_2$O): δ 1.23 (q, 3H), 1.27 (s, 18H), 2.39 (s, 4H), 2.86 (m, 16H), 3.39 (s, 4H), 4.11-4.16 (m, 4H). $^{13}$C NMR (400 MHz, D$_2$O): δ 14.0, 27.9, 51.6, 56.0, 60.3, 171.3, 173.5.

32

Synthesis of 3,3'-(4,10-bis(2-ethoxy-2-oxoethyl)-1,4,7,10-tetraazacyclododecane-1,7-diyl)dipropionic acid (10)

Compound 9 was dissolved in acetonitrile. Then 5 ml of TFA was added. The reaction mixture was stirred at room temperature overnight. The solvent was evaporated in vacuo and compound 10 was used for coupling reaction without further purification. $^1$H NMR (400 MHz, D$_2$O): δ 1.23 (q, 6H), 2.93 (t, 4H), 3.14-3.40 (m, 16H), 2.86 (m, 16H), 3.47-3.59 (m, 8H), 4.18 (m, 4H). $^{13}$C NMR (400 MHz, D$_2$O): δ 13.2, 27.9, 48.3, 50.0, 50.6, 62.4, 172.8, 173.6.

Scheme 3: Synthesis of Ligand 17 and the resultant metal chelated complex 18

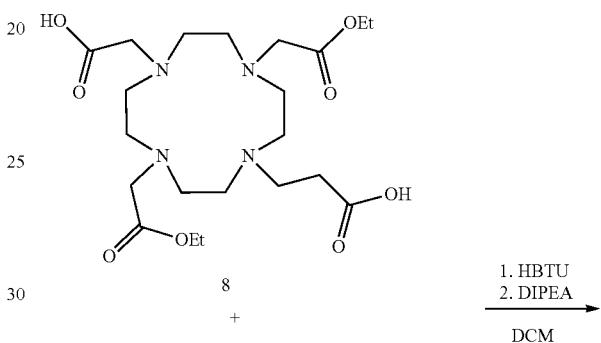

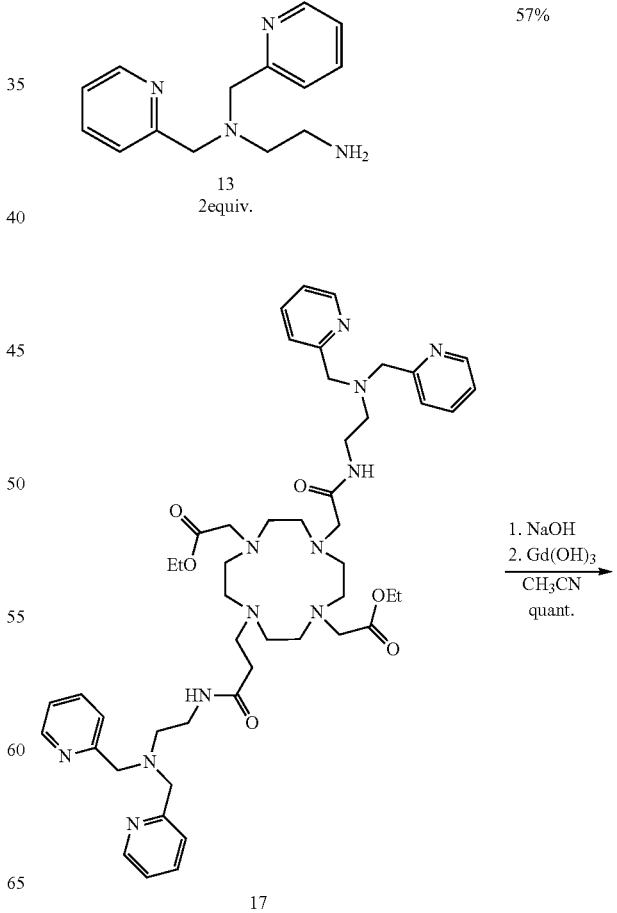

50.8, 53.5, 54.1, 55.2, 55.4, 126.4, 127.1, 141.4, 147.2, 152.5. LCMS-ESI: 1022.08 (M+H)+.

Scheme 4: Synthesis of Ligand 19 and the resultant metal chelated complex, 20

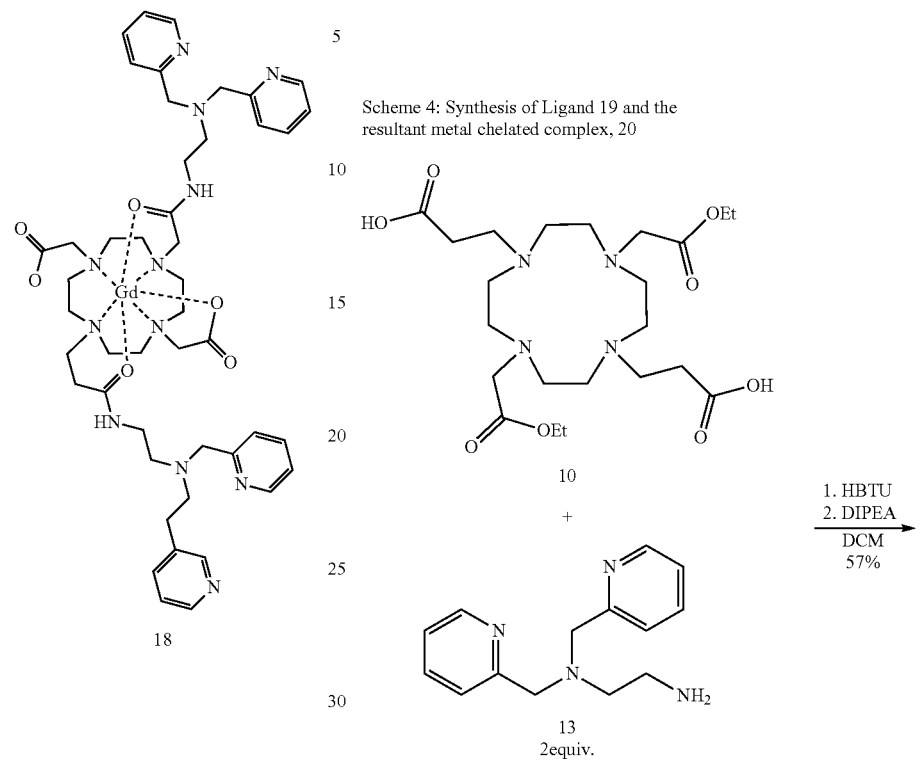

Synthesis of diethyl 2,2'-(4-(2-((2-(bis(pyridin-2-ylmethyl)amino)ethyl)amino)-2-oxoethyl)-10-(3-((2-(bis(pyridin-2-ylmethyl)amino)ethyl)amino)-3-oxo-propyl)-1,4,7,10-tetraazacyclododecane-1,7-diyl) diacetate (17)

2.0 g of compound 8 was added in 20 mL DMF resulting in a cloudy mixture, then 4 equiv. DIPEA were added in the mixture, then the reaction mixture become clear. 2 equiv. HBTU was added and the mixture was stirred for 10 min. Then 2 equiv. compound 13 were added. The mixture was stirred overnight at 120° C. The mixture was dissolved in ethyl acetate, then wash with saturated potassium carbonate solution and sodium chloride solution. The organic phase was evaporated to get the raw product 17 (yield: ca. 60%).

Synthesis of 17-Gd(III) (18)

The raw ethyl acetate protected ligand 17 was dissolved in 30 mL MeOH and then 1M NaOH solution (30 mL) was added. The mixture was stirred at room temperature overnight. The pH of the solution was adjusted to neutral with HCl. The solution was evaporated to dryness for HPLC separation. $^1$H NMR (400 MHz, D$_2$O): δ 2.73 (s, 2H), 2.89 (m, 4H), 3.29 (m, 8H), 3.40 (m, 8H), 3.49 (m, 2H), 3.67 (s, 4H), 3.94 (s, 2H), 7.99-8.11 (m, 8H), 8.57-8.76 (m, 8H). $^{13}$C NMR (400 MHz, D$_2$O): δ 29.7, 36.5, 36.7, 49.1, 49.2, 49.9,

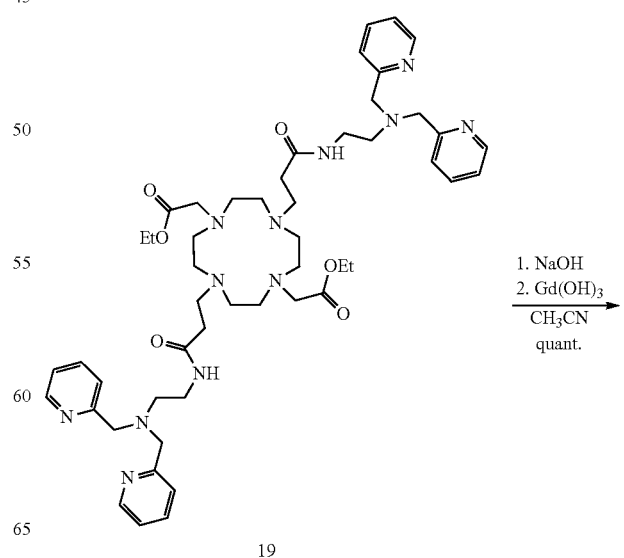

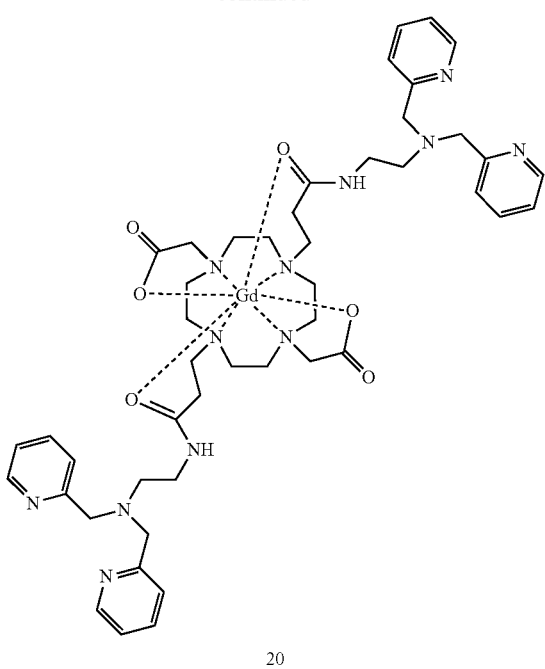

20

Synthesis of diethyl 2,2'-(4,10-bis(3-((2-(bis(pyridin-2-ylmethyl)amino)ethyl)amino)-3-oxopropyl)-1,4,7,10-tetraaza-cyclododecane-1,7-diyl)diacetate (19)

2.0 g of compound 10 was added in 20 mL DMF resulting in a cloudy mixture, then 4 equivalents of DIPEA was added in the mixture, then the reaction mixture become clear. 2 equiv HBTU was added and the mixture was stirred for 10 min, then 2 equiv. compound 13 was added. The mixture was stirred overnight at 120° C. The mixture was dissolved in ethyl acetate, then wash with saturated $K_2CO_3$ solution and NaCl. The organic phase was evaporated to get the raw product 17 (Yield: approximately 60%).

Synthesis of 19-Gd(III) (20)

The raw ethyl acetate protected ligand 19 was dissolved in 30 mL MeOH and then 1M NaOH solution (30 mL) was added. The mixture was stirred at room temperature overnight. The pH of the solution was adjusted to neutral with HCl. The solution was evaporated to dryness for HPLC separation. (Yield: 2.6 g, 67%) After separation using preparative HPLC, the pure compound 20 was obtained. $^1$H NMR (400 MHz, $D_2O$): δ 2.80 (m, 4H), 2.89 (m, 4H), 3.15-3.21 (m, 16H), 3.43 (m, 4H), 3.53 (s, 4H), 4.34 (s, 8H), 7.99-8.11 (m, 8H), 8.57-8.76 (m, 8H). $^{13}$C NMR (400 MHz, $D_2O$): δ 28.8, 36.6, 48.8, 50.2, 53.4, 54.2, 55.3, 126.4, 127.1, 141.4, 147.2, 152.5, 171.4, 174.8. LCMS-ESI: 1036.09 $(M+H)^+$.

Scheme 5: Synthesis of Zinc Chelating Unit 14

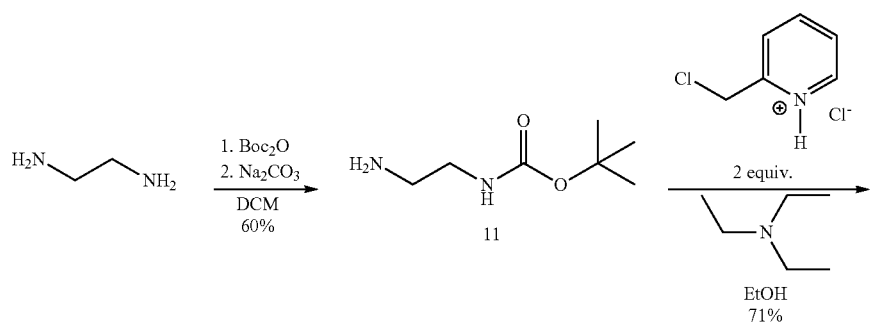

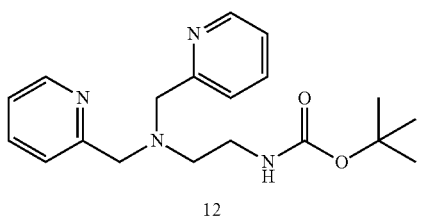

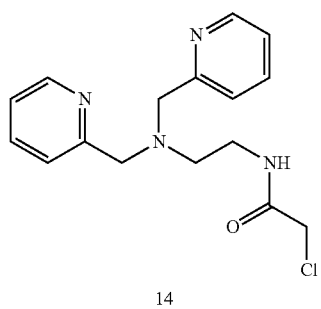
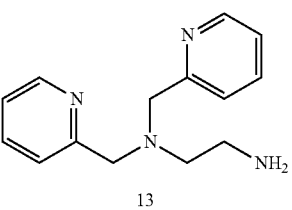

Synthesis of N¹,N¹-bis(pyridin-2-ylmethyl)ethane-1, 2-diamine (13)

This compound was synthesized according to published procedures. Only modification: pure product (13) was obtained upon chromatographic purification (silica, 100% ethyl acetate, product fraction elutes with 30-40% methanol/ 60-70% ethyl acetate). For synthetic procedure, see, Kiyose, et al., 2006, which is incorporated herein by reference. $^1$H NMR (300 MHz, CDCl$_3$): δ 1.94 (s, 2H), 2.66 (t, 2H), 2.82 (t, 2H), 3.85 (s, 4H), 7.12 (m, 2H), 7.49 (d, 2H), 7.63 (td, 2H), 8.52 (dd, 2H). $^{13}$C NMR (75 MHz, CDCl$_3$): δ 39.1, 56.7, 60.1, 121.5, 122.5, 135.9, 148.5, 159.1. HRMS (ESI+): calcd 243.1577, found 243.1609 (M+H)$^+$.

Synthesis of N-(2-(bis(pyridin-2-ylmethyl)amino) ethyl)-2-chloroacetamide (14)

N¹,N¹-bis(pyridin-2-ylmethyl)ethane-1,2-diamine (13, 12.70 g, 52.41 mmol) was dissolved in 100 mL dichloromethane. The deep red solution was cooled to 0° C. using an ice bath. Chloroacetyl chloride (6.215 g, 55.03 mmol) dissolved in 100 mL dichloromethane was added dropwise over the course of three hours. The reaction mixture was allowed to slowly warm up to room temperature and was stirred for another 16 hours. The solvent was evaporated in vacuo and 150 mL of diethyl ether was added to the brownish oily residue. This leads to the precipitation of product. Diethyl ether was decanted off and the grey precipitate was repeatedly washed with diethyl ether (5×100 mL). The product was further purified through column chromatography (silica, 95% chloroform/5% methanol to remove apolar impurities, the product fraction elutes upon gradual increase of eluent polarity with 40% chloroform/ 59% methanol/1% triethylamine). Yield: 15.54 g (48.74, 93%)$^1$H NMR (300 MHz, CDCl$_3$): δ 2.64 (t, 2H), 3.41 (t, 2H), 4.42 (s, 4H), 4.95 (s, 2h), 7.24-7.44 (m, 6H), 8.78 (d, 2H), 10.49 (br, 1H). LCMS-ESI: 319.81 (M+H)$^+$.

Scheme 6: Synthesis of Ligand 15 and the resultant metal chelated complex, 16

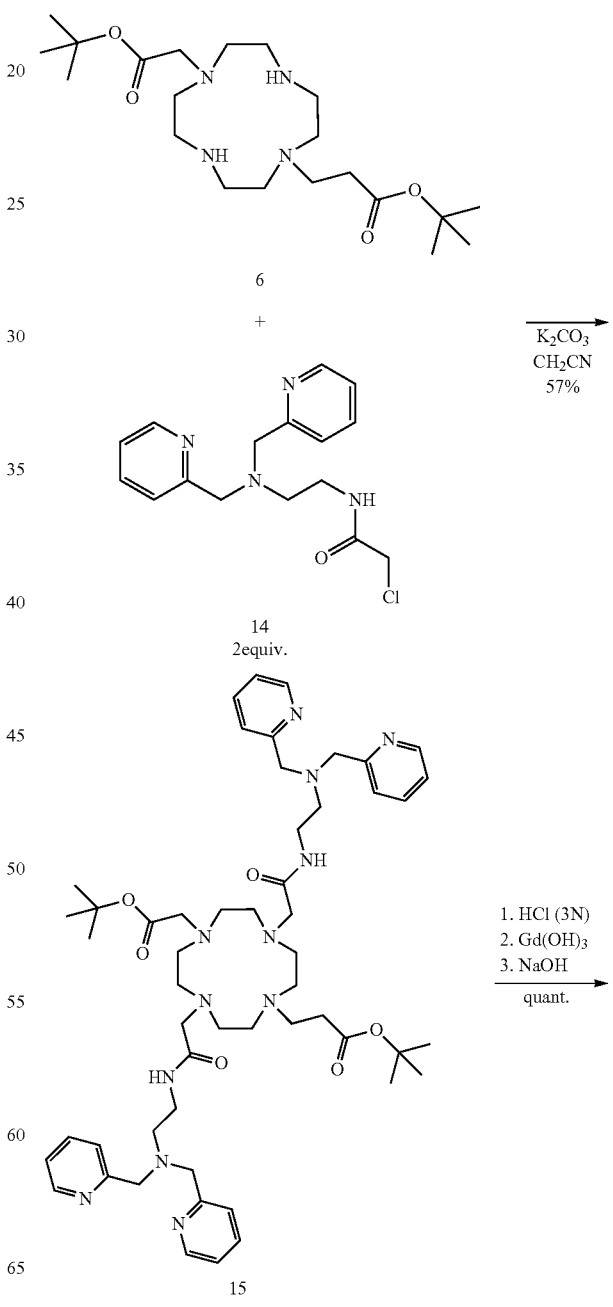

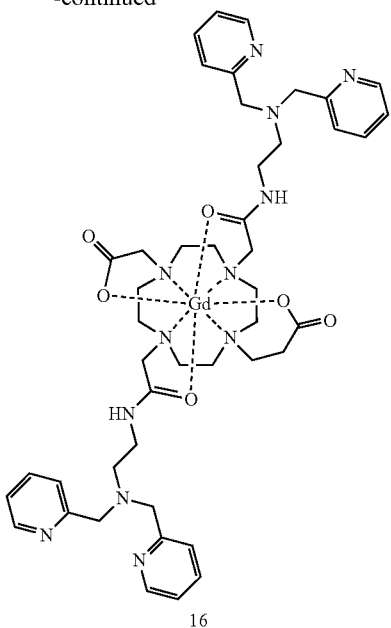

16

Synthesis of tert-butyl 3-(4,10-bis(2-((2-(bis(pyridin-2-ylmethyl)amino)ethyl)amino)-2-oxoethyl)-7-(2-(tert-butoxy)-2-oxoethyl)-1,4,7,10-tetraazacyclododecan-1-yl)propanoate (15)

Tert-butyl 3-(7-(2-(tert-butoxy)-2-oxoethyl)-1,4,7,10-tetraazacyclododecan-1-yl)propanoate (6, 5.86 g, 14.07 mmol) was suspended in 100 mL acetonitrile. N-(2-(bis(pyridin-2-ylmethyl)amino)ethyl)-2-chloroacetamide (14, 11 g, 30.96 mmol), together with potassium carbonate (21.4 g, 154.8 mmol), were added. The volume was increased to 250 mL and the suspension was refluxed at 63° C. for 48 hours. The solvent was removed in vacuo and the red-brown sludge was redissolved in dichloromethane, filtered and concentrated. Column chromatography (alumina, 97.8% chloroform/2% methanol/0.2% triethylamine) afforded the product that elutes as a yellow/orange fraction. After evaporation, the product was obtained as an orange oil in high purity. Without further characterization the product was used immediately in the next step. Yield: 7.85 g (8.02 mmol, 57%)

Synthesis of 15-Gd(III) (16)

Tert-butyl 3-(4,10-bis(2-((2-(bis(pyridin-2-ylmethyl)amino)ethyl)amino)-2-oxoethyl)-7-(2-(tert-butoxy)-2-oxoethyl)-1,4,7,10-tetraazacyclododecan-1-yl)propanoate (15, 5 g, 5.1 mmol) was dissolved in 100 mL 3N HCl. The deep red solution was stirred at room temperature for five days. After lyophilization, 9 g of intermediate (HCl salt) were dissolved in 100 mL water. Gadolinium(III) chloride hexahydrate (4.32 g, 11.51 mmol) was dissolved n 10 mL water and sodium hydroxide (14 g, 350 mmol) was added. The off white precipitate (gadolinium hydroxide hydrate) was filtered off and washed with water multiple times. The resulting gel-like white solid was added in one portion to the intermediate (HCl salt) of the intermediate described above. Upon stirring at room temperature, all solid slowly dissolved at which point the pH of the solution was adjusted to pH=5 through slow addition of solid sodium hydroxide. The reaction mixture was stirred for 3 days at room temperature. The pH was adjusted to 9 and the off white precipitate was filtered off. The product was obtained as a pale yellow solid upon lyophilization and preparative HPLC purification (preparative tC18 column, increasing acetonitrile concentration (2% to 20%) in triethylammonium acetate buffer (pH=7)). Yield: 5.21 g (5.1 mmol, quant.) LCMS-ESI: 511.6713 $(M)^{2+}$, 1022.2013 $(M+H)^+$.

Scheme 7: Homologated Dipyridine Complex 5

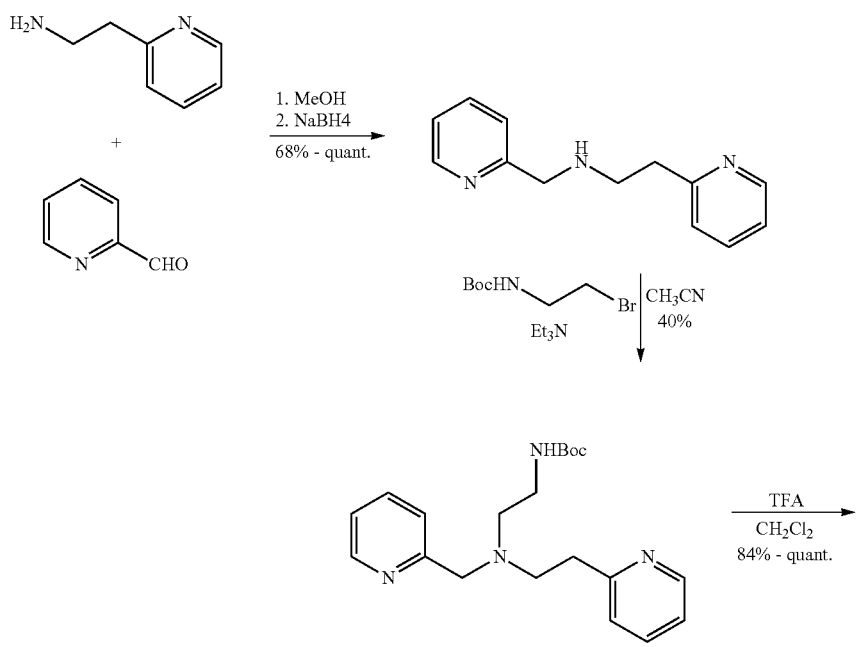

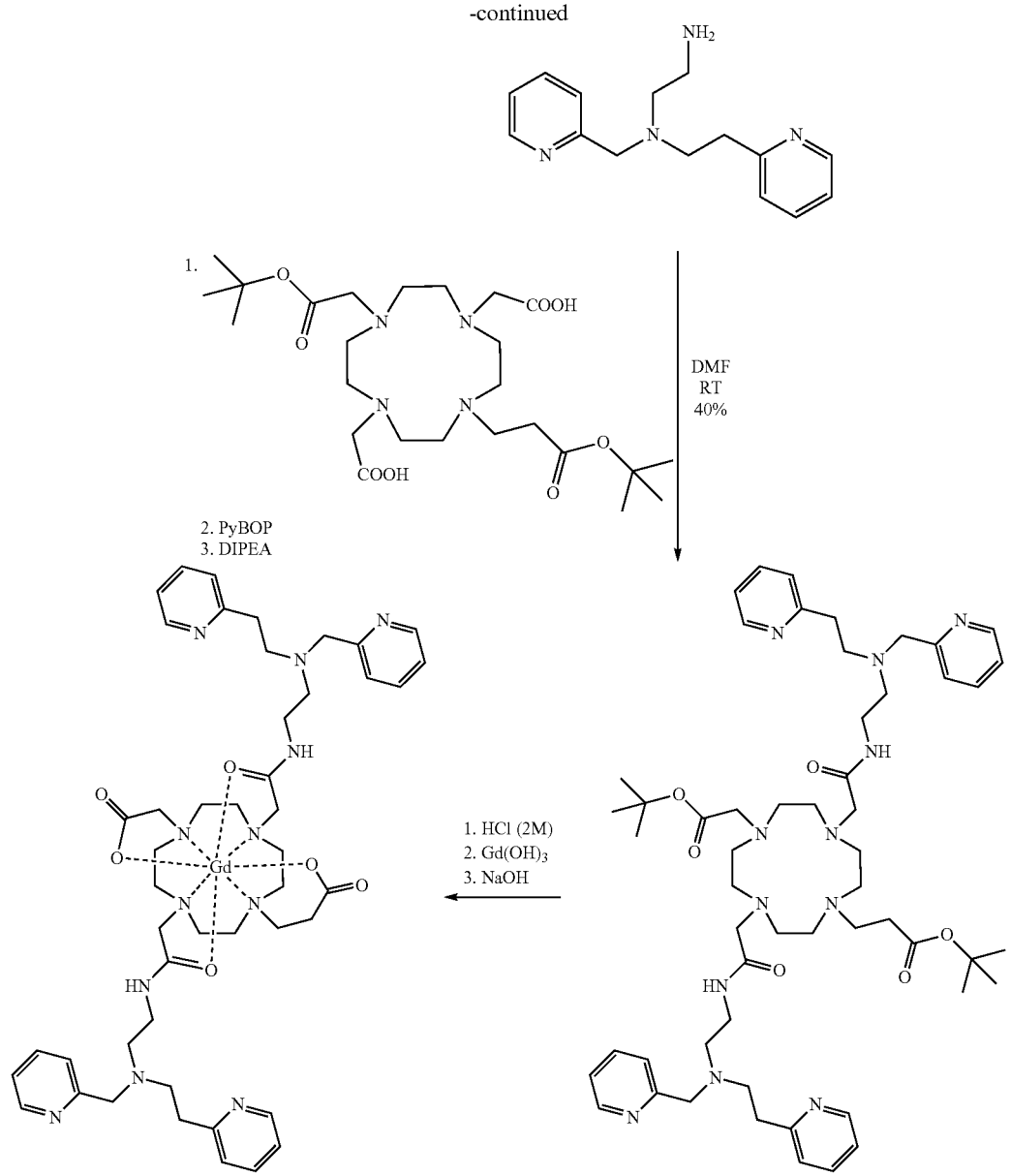

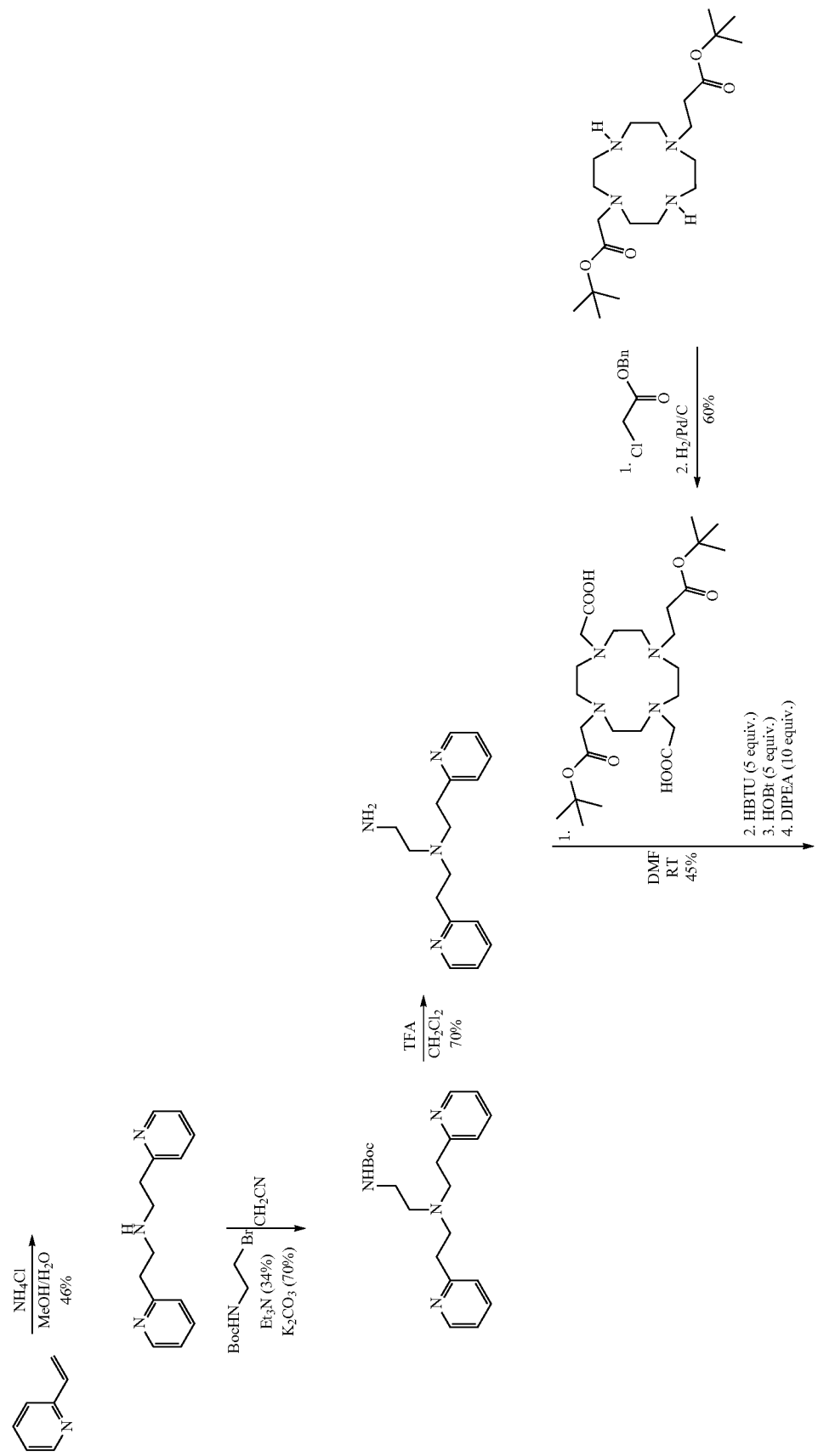

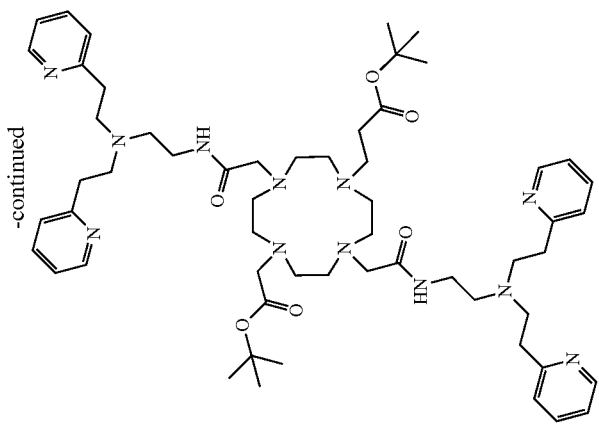
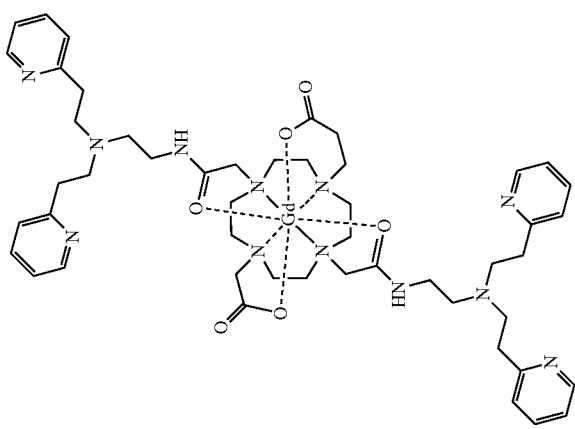

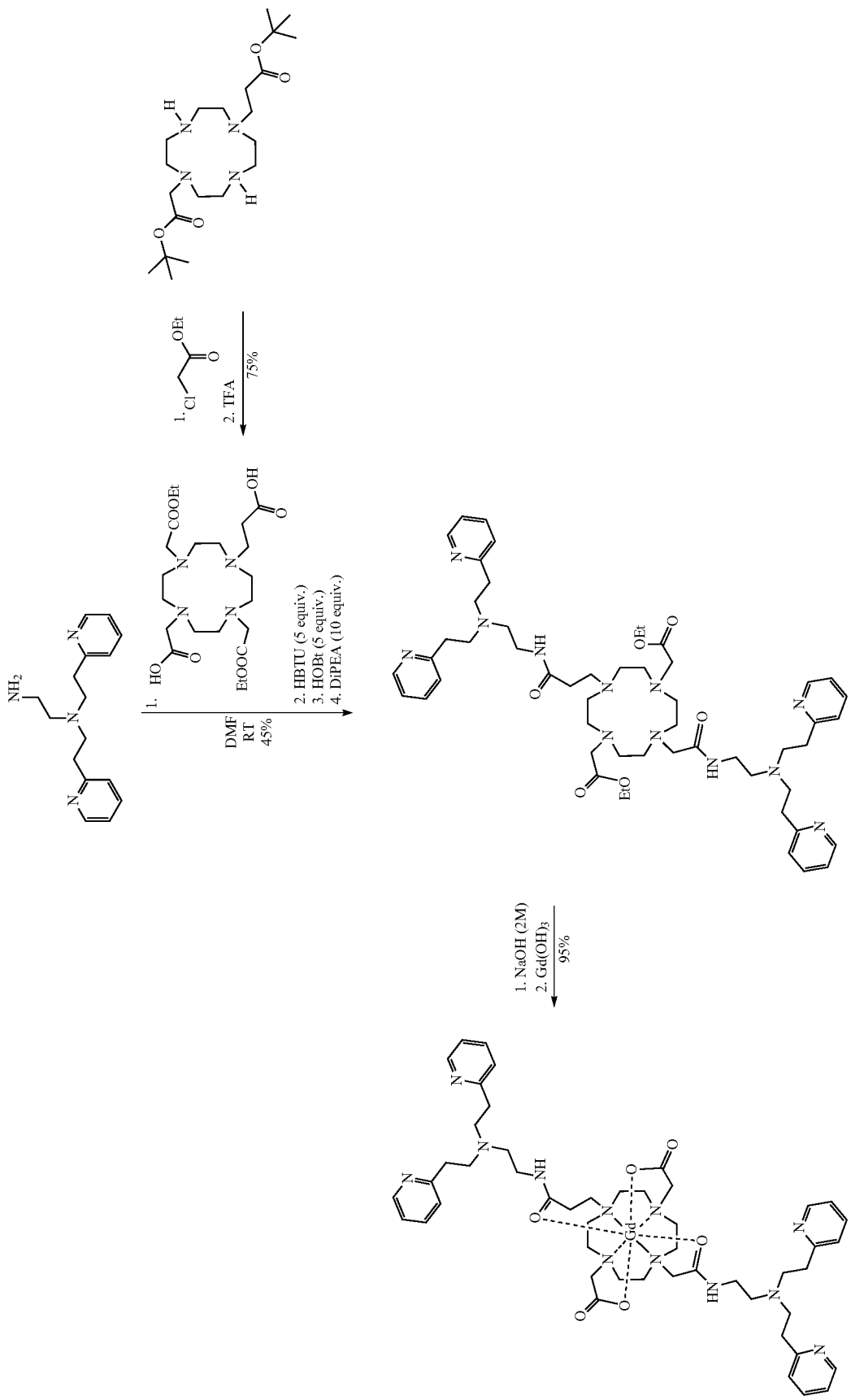
Scheme 9: Doubly Homologated Dipyridine Complex 7

Example 2—Relaxivity Studies

The new imaging agents were tested to identify their relaxivity and contrast enhancement compared to compound described by Esqueda, et al. (2009). The results of these relaxivity studies are summarized in Table 2.

TABLE 2

Relaxivity Measurements (0.47 T, 23 MHz) of GdDOTA-diBPEN 1 in comparison with the compounds of the present disclosure

| Complex | $r_1$ Complex ($mM^{-1}s^{-1}$) | $r_1$ Complex + 2 Zn(II) ($mM^{-1}s^{-1}$) | $r_1$ Complex + 2 Zn(II) + HSA ($mM^{-1}s^{-1}$) | $r_1$ Complex + 2 Zn(II) + HSA/$r_1$ Complex | $r_1$ Complex + 2 Zn(II) + HSA/$r_1$ Complex + 2 Zn(II) | Contrast Enhancement (%) |
|---|---|---|---|---|---|---|
| 1 | 5.0 | 6.6 | 17.4 | 3.48 | 2.63 | 163 |
| 2 | 6.1 | 6.6 | 51.3 | 8.41 | 7.77 | 677 |
| 3 | 6.7 | 7.1 | 57.3 | 8.55 | 8.07 | 707 |
| 4 | 4.1 | 3.4 | 15.6 | 3.80 | 4.60 | 360 |

All of the compositions and methods disclosed and claimed herein can be made and executed without undue experimentation in light of the present disclosure. While the compositions and methods of this disclosure have been described in terms of certain embodiments, it will be apparent to those of skill in the art that variations may be applied to the compositions and methods and in the steps or in the sequence of steps of the methods described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

E. REFERENCES

The following references, to the extent that they provide exemplary procedural or other details supplementary to those set forth herein, are specifically incorporated herein by reference.

PCT Application WO 2002/043775
U.S. Patent Publication No. 2011/0009605
Caravan, et al., *Chemical Reviews*, 99:2293-2352, 1999.
Caravan, *Chemical Society Reviews*, 35:512-523, 2006.
Esqueda, et al., *J. Am. Chem. Soc.*, 131:11387-11391, 2009.
*Handbook of Pharmaceutical Salts: Properties, and Use*, Stahl and Wermuth Eds.),
Verlag Helvetica Chimica Acta, 2002.
Hirayama, et al., *Chem. Commun.*, 22:3196-3198, 2009
Huang, et al., *Biomaterials*, 32:5177-5186, 2011.
Kiyose, et al., *J. Am. Chem. Soc.* 128:6548-6549, 2006.
*March's Advanced Organic Chemistry: Reactions, Mechanisms, and Structure*, 2007.
Rohrer, et al., *Investigative Radiology*, 40:715-724, 2005.
Shiraishi, et al., *Journal of Controlled Release*, 148:160-167, 2010.
Weissleder, *Science*, 312:1168-1171, 2006.
Woods and Sherry, *Inorg. Chem.*, 42:4401-4408, 2003.

What is claimed:

1. A compound of the formula:

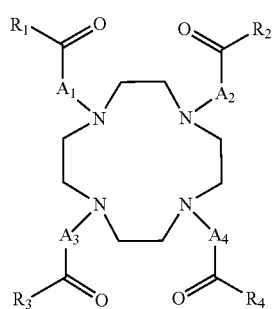

wherein:
A1, A2, A3, and A4 are each independently alkanediyl$_{(C \leq 12)}$ or substituted alkanediyl$_{(c<12)}$; and
$R_1$, $R_2$, $R_3$, and $R_4$ are each independently hydroxy, or

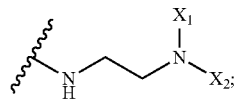

provided at least one $R_1$, $R_2$, $R_3$ and $R_4$ is

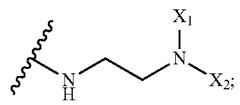

wherein:
$X_1$ and $X_2$ are each independently heteroaralkyl$_{(C \leq 12)}$ or substituted heteroaralkyl$_{(C \leq 12)}$;
provided that at least one of A1, A2, A3, or A4 is not —$CH_2$—;
or a metal complex, a deprotonated form, or a salt thereof.

2. The compound of claim 1, wherein the compound is further defined as:

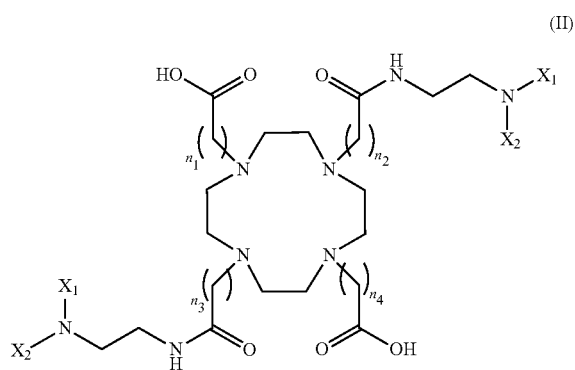

(II)

wherein:
 $n_1$, $n_2$, $n_3$, and $n_4$ are 1, 2, 3, 4, 5, 6, 7, or 8; and
 $X_1$ and $X_2$ are each independently selected from heteroaralkyl$_{(C≤12)}$ or substituted heteroaralkyl$_{(C≤12)}$;
 provided that at least one of $n_1$, $n_2$, $n_3$, and $n_4$ are not 1;
or a metal complex, a deprotonated form or a salt thereof.

3. The compound of claim 1, wherein the compound is further defined as:

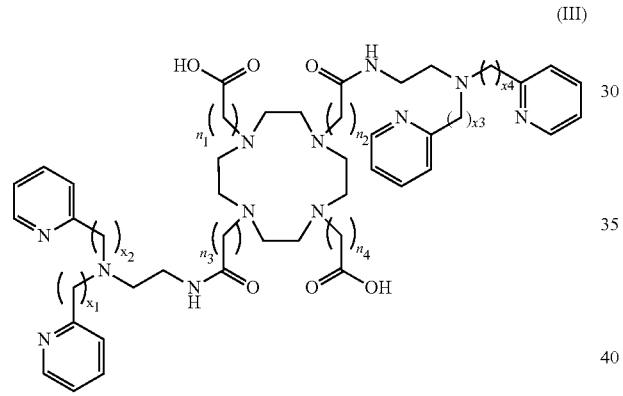

(III)

wherein:
 $n_1$, $n_2$, $n_3$, and $n_4$ are 1, 2, 3, or 4; provided that at least one of $n_1$, $n_2$, $n_3$, and $n_4$ are not 1; and
 $x_1$, $x_2$, $x_3$, and $x_4$ are 1, 2, 3, or 4;
or a metal complex, a deprotonated form, or a salt thereof.

4. The compound of claim 1, wherein the compound is a metal complex and further comprises a metal ion chelated as defined by the formula:

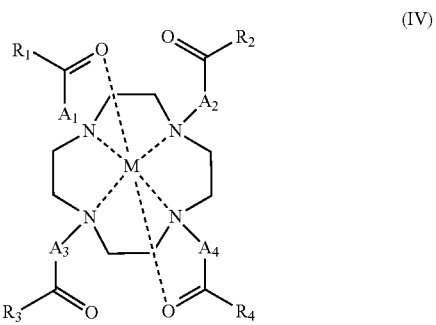

(IV)

wherein:
 $A_1$, $A_2$, $A_3$, $A_4$, $R_1$, $R_2$, $R_3$, $R_4$ are as defined above; and
 M is a metal ion;
or a deprotonated form or a salt thereof.

5. The compound of claim 4, wherein M is $Mn^{2+}$, $Mn^{3+}$, or a lanthanide ion.

6. The compound of claim 1, further defined as a metal complex of the formula:

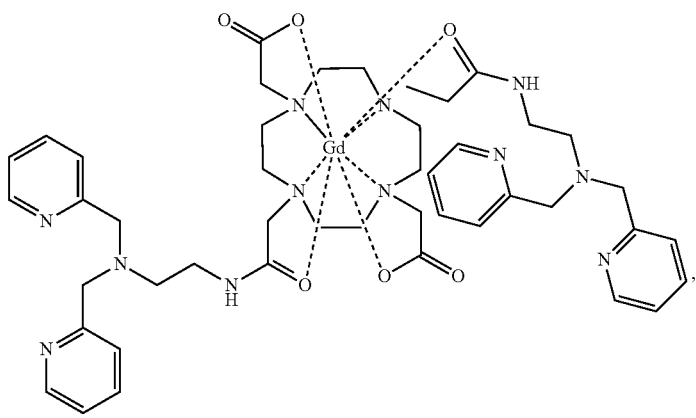

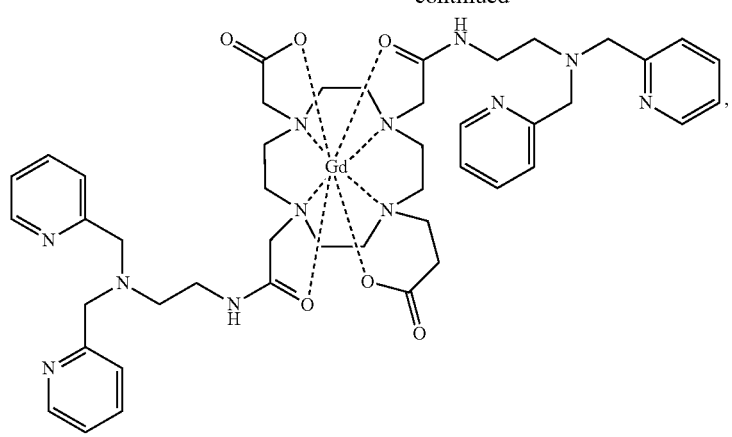
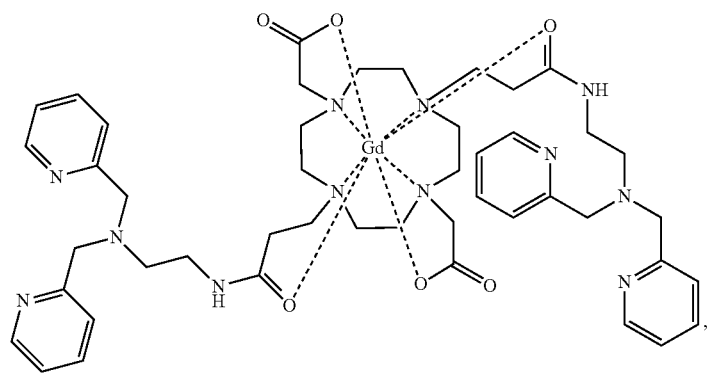
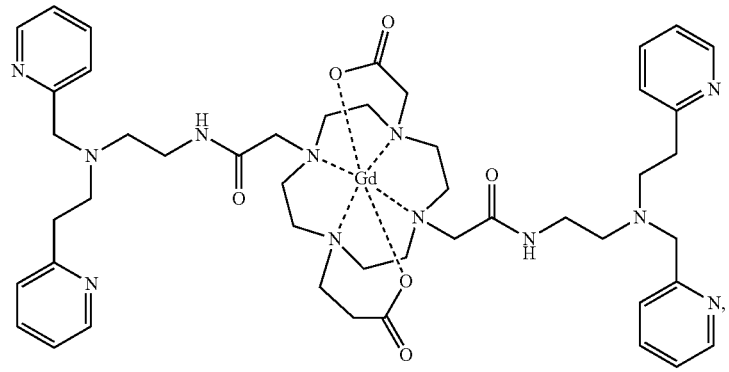
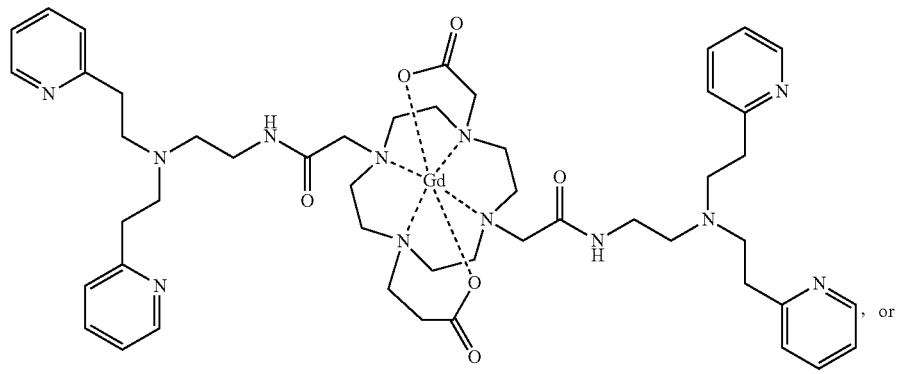

-continued

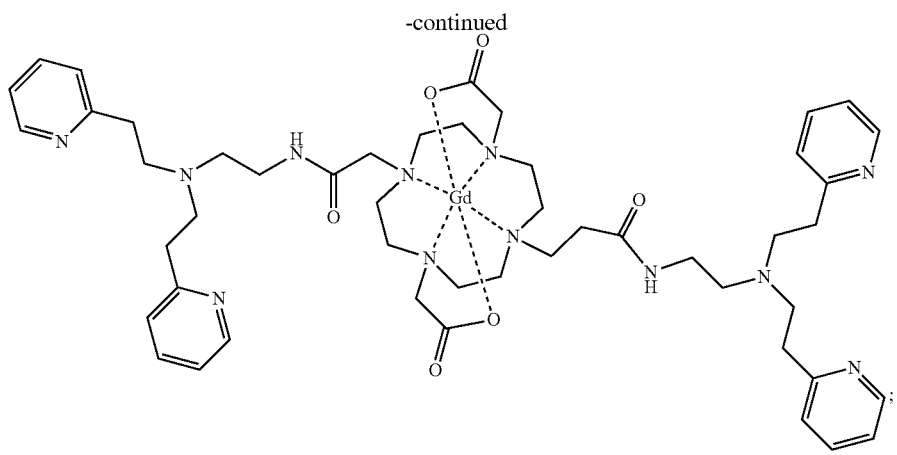

or a deprotonated form or a salt thereof.

7. A pharmaceutical composition comprising a compound of claim 1 and a pharmaceutically acceptable carrier.

8. A method of imaging a patient comprising the steps of:
a) administering to the patient a compound of claim 1; and
b) obtaining an imaging scan of the patient.

9. The method of claim 8, wherein the collected imaging scan is from an MRI.

10. The method of claim 8, further comprising analyzing the imaging scan.

11. The method of claim 8, wherein analyzing the imaging scan produces a diagnosis of a disease.

12. A method of imaging the pancreas in vivo in a patient to determine the onset of β-cell degeneration comprising the steps of:

a) administering to the patient a compound of claim 1;
b) obtaining an imaging scan of the patient; and
c) determining the presence of $Zn^{2+}$ ions.

13. The method of claim 12, wherein the imaging scan is from an MRI.

14. The method of claim 12, wherein the onset of β-cell degeneration indicates the onset of diabetes mellitus.

15. A method of imaging the prostate in vivo in a patient to determine the presence of a prostate tumor comprising the steps of:
a) administering to the patient a compound of claim 1;
b) obtaining an imaging scan of the patient; and
c) determining the presence of $Zn^{2+}$ ions.

16. The method of claim 15, wherein the imaging scan is from an MRI.

* * * * *